US009888862B2

(12) United States Patent
Harlev et al.

(10) Patent No.: US 9,888,862 B2
(45) **Date of Patent: *Feb. 13, 2018**

(54) ELECTROANATOMICAL MAPPING

(71) Applicant: Boston Scientific Scimed, Inc., Maple Grove, MN (US)

(72) Inventors: Doron Harlev, Brookline, MA (US); Brian Stewart, North Reading, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/338,523

(22) Filed: Oct. 31, 2016

(65) Prior Publication Data

US 2017/0042436 A1 Feb. 16, 2017

Related U.S. Application Data

(63) Continuation of application No. 14/809,858, filed on Jul. 27, 2015, now Pat. No. 9,498,146, which is a (Continued)

(51) Int. Cl.

*A61B 5/042* (2006.01)
*A61B 5/053* (2006.01)
(Continued)

(52) U.S. Cl.

CPC .............. *A61B 5/044* (2013.01); *A61B 5/042* (2013.01); *A61B 5/04012* (2013.01); *A61B 5/0452* (2013.01); *A61B 5/0536* (2013.01); *A61B 5/6852* (2013.01); *A61B 5/742* (2013.01); *A61B 5/743* (2013.01); *A61B 18/00* (2013.01); *G06F 19/322* (2013.01); *G06F 19/345* (2013.01); *G06F 19/3487* (2013.01); *G06T 19/00* (2013.01); *A61B 5/0402* (2013.01); *A61B 5/0422* (2013.01); *A61B 5/055* (2013.01); *A61B 5/4836* (2013.01); *A61B 5/7203* (2013.01);
(Continued)

(58) Field of Classification Search
None
See application file for complete search history.

(56) References Cited

U.S. PATENT DOCUMENTS

| | | | |
|---|---|---|---|
| 1,674,518 | A | 6/1928 | Parsons |
| 2,939,309 | A | 6/1960 | Sitton |

(Continued)

FOREIGN PATENT DOCUMENTS

| | | | |
|---|---|---|---|
| JP | H09508293 | A | 8/1997 |
| JP | H10234693 | A | 9/1998 |

(Continued)

OTHER PUBLICATIONS

Reddy et al., "Integration of Cardiac Meagnetic Resonance Imaging with Three-Dimentional Electroanatomic Mapping to Guide Left Ventricular Catheter Manipulation—Feasibility is a Porcine Modelof Healed Myocardial Infarction", Journal of the American College of Cardiology, 44(11):2202-2213, 2004.

(Continued)

*Primary Examiner* — Brian T Gedeon
(74) *Attorney, Agent, or Firm* — Faegre Baker Daniels LLP

(57) ABSTRACT

This invention relates to the determination and/or representation of physiological information relating to a heart surface.

20 Claims, 14 Drawing Sheets

Related U.S. Application Data continuation of application No. 13/717,856, filed on Dec. 18, 2012, now Pat. No. 9,107,599, which is a continuation of application No. 13/182,830, filed on Jul. 14, 2011, now Pat. No. 8,428,700.

(60) Provisional application No. 61/432,404, filed on Jan. 13, 2011.

(51) Int. Cl.

| | |
|---|---|
| ***A61B 5/04*** | (2006.01) |
| ***G06T 19/00*** | (2011.01) |
| ***A61B 5/044*** | (2006.01) |
| ***G06F 19/00*** | (2011.01) |
| ***A61B 18/00*** | (2006.01) |
| ***A61B 5/0452*** | (2006.01) |
| *A61B 5/0402* | (2006.01) |
| *A61B 5/055* | (2006.01) |
| *A61B 6/00* | (2006.01) |
| *A61B 5/00* | (2006.01) |

(52) U.S. Cl.

CPC ........... *A61B 5/7242* (2013.01); *A61B 5/7475* (2013.01); *A61B 6/00* (2013.01); *A61B 2560/0295* (2013.01); *G06T 2219/004* (2013.01)

(56) References Cited

U.S. PATENT DOCUMENTS

| | | | |
|---|---|---|---|
| 4,649,924 | A | 3/1987 | Taccardi |
| 4,674,518 | A | 6/1987 | Salo |
| 4,840,182 | A | 6/1989 | Carlson |
| 4,920,490 | A | 4/1990 | Isaacson |
| 4,964,410 | A | 10/1990 | Leahey et al. |
| 5,156,151 | A | 10/1992 | Imran |
| 5,284,142 | A | 2/1994 | Goble et al. |
| 5,297,549 | A | 3/1994 | Beatty et al. |
| 5,300,068 | A | 4/1994 | Rosar et al. |
| 5,341,807 | A | 8/1994 | Nardella |
| 5,381,333 | A | 1/1995 | Isaacson et al. |
| 5,469,858 | A | 11/1995 | Osborne |
| 5,480,422 | A | 1/1996 | Ben-Haim |
| 5,500,011 | A | 3/1996 | Desai |
| 5,553,611 | A | 9/1996 | Budd et al. |
| 5,568,809 | A | 10/1996 | Ben-Haim |
| 5,577,502 | A | 11/1996 | Darrow et al. |
| 5,588,429 | A | 12/1996 | Isaacson et al. |
| 5,634,469 | A | 6/1997 | Bruder et al. |
| 5,662,108 | A | 9/1997 | Budd et al. |
| 5,687,737 | A | 11/1997 | Branham et al. |
| 5,697,377 | A | 12/1997 | Wittkampf |
| 5,704,365 | A | 1/1998 | Albrecht et al. |
| 5,711,305 | A | 1/1998 | Swanson et al. |
| 5,722,402 | A | 3/1998 | Swanson et al. |
| 5,724,985 | A | 3/1998 | Snell et al. |
| 5,810,740 | A | 9/1998 | Paisner |
| 5,840,025 | A | 11/1998 | Ben-Haim |
| 5,840,031 | A | 11/1998 | Crowley |
| 5,846,198 | A | 12/1998 | Killmann |
| 5,848,972 | A | 12/1998 | Triedman et al. |
| 5,921,982 | A | 7/1999 | Lesh et al. |
| 5,954,665 | A | 9/1999 | Ben-Haim |
| 5,971,933 | A | 10/1999 | Gopakumaran et al. |
| 5,983,126 | A | 11/1999 | Wittkampf |
| 6,014,581 | A | 1/2000 | Whayne et al. |
| 6,050,267 | A | 4/2000 | Nardella et al. |
| 6,095,150 | A | 8/2000 | Panescu et al. |
| 6,167,296 | A | 12/2000 | Shahidi |
| 6,226,542 | B1 | 5/2001 | Reisfeld |
| 6,236,883 | B1 | 5/2001 | Ciaccio et al. |
| 6,236,886 | B1 | 5/2001 | Cherepenin et al. |
| 6,240,307 | B1 | 5/2001 | Beatty et al. |
| 6,246,898 | B1 | 6/2001 | Vesely et al. |
| 6,254,536 | B1 | 7/2001 | DeVito |
| 6,278,894 | B1 | 8/2001 | Salo et al. |
| 6,298,257 | B1 | 10/2001 | Hall et al. |
| 6,308,093 | B1 | 10/2001 | Armoundas et al. |
| 6,314,310 | B1 | 11/2001 | Ben-Haim et al. |
| 6,317,619 | B1 | 11/2001 | Boernert et al. |
| 6,318,375 | B1 | 11/2001 | Plicchi et al. |
| 6,360,123 | B1 | 3/2002 | Kimchi et al. |
| 6,368,285 | B1 | 4/2002 | Osadchy et al. |
| 6,400,981 | B1 | 6/2002 | Govari |
| 6,516,807 | B1 | 2/2003 | Panescu et al. |
| 6,547,082 | B1 | 4/2003 | Babini |
| 6,556,695 | B1 | 4/2003 | Packer et al. |
| 6,574,492 | B1 | 6/2003 | Ben-Haim et al. |
| 6,574,498 | B1 | 6/2003 | Gilboa |
| 6,593,884 | B1 | 7/2003 | Gilboa et al. |
| 6,599,241 | B1 | 7/2003 | Murphy |
| 6,600,948 | B2 | 7/2003 | Ben-Haim et al. |
| 6,603,996 | B1 | 8/2003 | Beatty et al. |
| 6,631,290 | B1 | 10/2003 | Guck et al. |
| 6,640,119 | B1 | 10/2003 | Budd et al. |
| 6,650,927 | B1 | 11/2003 | Keidar |
| 6,690,963 | B2 | 2/2004 | Ben-Haim et al. |
| 6,701,176 | B1 | 3/2004 | Halperin et al. |
| 6,728,562 | B1 | 4/2004 | Budd et al. |
| 6,773,402 | B2 | 8/2004 | Govari et al. |
| 6,807,439 | B2 | 10/2004 | Edwards et al. |
| 6,839,588 | B1 | 1/2005 | Rudy |
| 6,847,839 | B2 | 1/2005 | Ciaccio et al. |
| 6,872,428 | B2 | 3/2005 | Yang et al. |
| 6,892,090 | B2 | 5/2005 | Verard et al. |
| 6,892,091 | B1 | 5/2005 | Ben-Haim et al. |
| 6,939,309 | B1 | 9/2005 | Beatty et al. |
| 6,957,101 | B2 | 10/2005 | Porath et al. |
| 6,978,168 | B2 | 12/2005 | Beatty et al. |
| 6,990,370 | B1 | 1/2006 | Beatty et al. |
| 7,016,719 | B2 | 3/2006 | Rudy et al. |
| 7,043,292 | B2 | 5/2006 | Tarjan et al. |
| 7,263,397 | B2 | 8/2007 | Hauck et al. |
| 7,505,810 | B2 | 3/2009 | Harlev et al. |
| 7,515,954 | B2 | 4/2009 | Harlev et al. |
| 7,599,730 | B2 | 10/2009 | Hunter et al. |
| 7,706,867 | B1 | 4/2010 | Ostrow |
| 7,709,867 | B2 | 5/2010 | Ishikawa et al. |
| 7,729,752 | B2 | 6/2010 | Harlev et al. |
| 7,856,260 | B1 | 12/2010 | Ryu |
| 8,021,361 | B2 | 9/2011 | Paul et al. |
| 8,103,327 | B2 | 1/2012 | Harlev et al. |
| 8,103,338 | B2 | 1/2012 | Harlev et al. |
| 8,137,343 | B2 | 3/2012 | Harlev et al. |
| 8,182,433 | B2 | 5/2012 | Leo et al. |
| 8,267,926 | B2 | 9/2012 | Paul et al. |
| 8,357,152 | B2 | 1/2013 | Govari et al. |
| 9,289,148 | B2 | 3/2016 | Harlev et al. |
| 2002/0091333 | A1 | 7/2002 | Hsu et al. |
| 2002/0151807 | A1 | 10/2002 | Goldin |
| 2002/0177421 | A1 | 11/2002 | Muhammad et al. |
| 2003/0018251 | A1 | 1/2003 | Solomon |
| 2003/0065271 | A1 | 4/2003 | Khoury |
| 2003/0076277 | A1 | 4/2003 | Muramatsu et al. |
| 2003/0078509 | A1 | 4/2003 | Panescu |
| 2003/0216630 | A1 | 11/2003 | Jersey-Willuhn et al. |
| 2004/0039293 | A1 | 2/2004 | Porath et al. |
| 2004/0077942 | A1 | 4/2004 | Hall et al. |
| 2004/0097806 | A1 | 5/2004 | Hunter et al. |
| 2004/0127805 | A1 | 7/2004 | MacAdam et al. |
| 2004/0243015 | A1 | 12/2004 | Smith et al. |
| 2004/0254437 | A1 | 12/2004 | Hauck et al. |
| 2005/0038337 | A1 | 2/2005 | Edwards |
| 2005/0054918 | A1 | 3/2005 | Sra |
| 2005/0107834 | A1 | 5/2005 | Freeman et al. |
| 2005/0154282 | A1 | 7/2005 | Li et al. |
| 2005/0288599 | A1 | 12/2005 | MacAdam et al. |
| 2006/0085049 | A1 | 4/2006 | Cory et al. |
| 2006/0116575 | A1 | 6/2006 | Willis |
| 2006/0122526 | A1 | 6/2006 | Berenfeld et al. |
| 2006/0173251 | A1 | 8/2006 | Govari et al. |
| 2006/0178587 | A1 | 8/2006 | Khoury |

(56) References Cited

U.S. PATENT DOCUMENTS

| | | | |
|---|---|---|---|
| 2006/0200049 | A1 | 9/2006 | Leo et al. |
| 2006/0241401 | A1 | 10/2006 | Govari et al. |
| 2007/0016007 | A1 | 1/2007 | Govari et al. |
| 2007/0038078 | A1 | 2/2007 | Osadchy |
| 2007/0049821 | A1 | 3/2007 | Willis |
| 2007/0073179 | A1 | 3/2007 | Afonso et al. |
| 2007/0083193 | A1 | 4/2007 | Werneth et al. |
| 2007/0100332 | A1 | 5/2007 | Paul et al. |
| 2007/0197929 | A1 | 8/2007 | Porath et al. |
| 2007/0265539 | A1 | 11/2007 | Hastings et al. |
| 2007/0270703 | A1 | 11/2007 | He et al. |
| 2007/0287902 | A1 | 12/2007 | Fuimaono et al. |
| 2007/0299351 | A1 | 12/2007 | Harlev et al. |
| 2007/0299352 | A1 | 12/2007 | Harlev et al. |
| 2008/0137927 | A1 | 6/2008 | Altmann et al. |
| 2008/0190438 | A1 | 8/2008 | Harlev et al. |
| 2008/0221566 | A1 | 9/2008 | Krishnan |
| 2008/0234588 | A1 | 9/2008 | Feldman et al. |
| 2008/0249424 | A1 | 10/2008 | Harlev et al. |
| 2008/0281319 | A1 | 11/2008 | Paul et al. |
| 2009/0069642 | A1 | 3/2009 | Gao et al. |
| 2009/0069704 | A1 | 3/2009 | MacAdam et al. |
| 2009/0093806 | A1 | 4/2009 | Govari et al. |
| 2009/0171274 | A1 | 7/2009 | Harlev et al. |
| 2009/0177072 | A1 | 7/2009 | Harlev et al. |
| 2009/0253976 | A1 | 10/2009 | Harlev et al. |
| 2009/0264767 | A1 | 10/2009 | Griffin et al. |
| 2009/0281439 | A1 | 11/2009 | Harlev et al. |
| 2010/0049069 | A1 | 2/2010 | Tarassenko et al. |
| 2010/0168620 | A1 | 7/2010 | Klimovitch et al. |
| 2010/0274150 | A1 | 10/2010 | Harlev et al. |
| 2010/0286550 | A1 | 11/2010 | Harlev et al. |
| 2010/0286551 | A1 | 11/2010 | Harlev et al. |
| 2010/0311482 | A1 | 12/2010 | Lange |
| 2012/0184684 | A1 | 7/2012 | Funk et al. |

FOREIGN PATENT DOCUMENTS

| | | | |
|---|---|---|---|
| JP | 2001070269 | A | 3/2001 |
| JP | 2005506097 | A | 3/2005 |
| JP | 2005131367 | A | 5/2005 |
| JP | 2007537823 | A | 12/2007 |
| JP | 2008536633 | A | 9/2008 |
| JP | 2009537252 | A | 10/2009 |
| JP | 2009539566 | A | 11/2009 |
| WO | 2005115232 | A1 | 12/2005 |
| WO | 2006113698 | A1 | 10/2006 |
| WO | 2007137077 | A2 | 11/2007 |
| WO | 2010020958 | A1 | 2/2010 |

OTHER PUBLICATIONS

Sanders et al., “Spectral Analysis Identifies Sites of High-Frequency Activity Maintaining Atrial Fibrillation in Humans”, Circulation, 112:789-797, 2005.

Sethian, “Level Set Methods and Fast Marching Methods: Evolving Interfaces in Computational Geometry, Fluid Mechanics, Computer Vision, and Materials Science”, Department of Mathematics-University of California, Berkeley, Cambridge University Press, 1999.

Smits et al., “Catheter-Based Intramyocarial Injection of Autologous Skeletal Myoblasts as a Primary Treatment of Ischemic Heart Failure”, Journal of the American College of Cardiology, 42(12):2063-2069, 2003.

Solomon et al., “Real-Time Cardiac Catheter Navigation on Three-Dimensional CT Images”, Journal of Interventional Cardiac Electrophysiology, 8:27-36, 2003.

Sra et al., “Registration of Three-Dimensional Left Atrial Computed Tomographic Images With Projection Images Obtained Using Fluoroscopy”, Circulation, 112:3763-3768, 2005.

Sra, Jasbir et al, “Registration of 3D Computed Tomographic Images With Interventional Systems: Implications for Catheter Ablation of Atrial Fibrillation”, J Interv Card Electrophysiol, 16:141-148, 2006.

Stevenson, “Radiofrequency Catheter Ablation of Ventricular Tachycardia After Myocardial Infarction”, Circulation, 98:308-314, 1998.

Taccardi et al., “A New Intracavitary Probe for Detecting the Site of the Origin of Ectopic Ventricular Beats During One Cardiac Cycle”, Circulation, 75(1):272-281, 1987.

Thal et al., “Novel Applications in Catheter Ablation”, Journal of Interventional Cardiac Electrophysiology, 13:17-21, 2005.

Thiagalingam et al., “Noncontact Mapping of the Left Ventricle: Insights from Validation With Transmural Contact Mapping”, PACE, 27:570-578, 2004.

U.S. Appl. No. 13/182,825, Harlev et al., filed Jul. 14, 2011.

U.S. Appl. No. 13/182,830, Harlev et al., filed Jul. 14, 2011.

U.S. Appl. No. 61/432,404, Harlev et al., filed Jan. 13, 2011.

Voth, “The Inverse Problem of Electrocardiography: Industrial Solutions and Simulations”, BEM and NFSI Conference Proceedings, Minneapolis, MN, May 12-15, 2005, pp. 191-194.

Wittkampf et al., “LocaLisa: New Technique for Real-Time 3-Dimensional Localization of Regular Intracardiac Electrodes”, Circulation, 99:1312-1317, 1999.

Yezzi, Anthony et al., “A Geometric Snake Model for Segmentation”, IEEE Transactions on Medical Imaging, 16(2) Apr. 1997.

Adams et al., “Seeded Region Growing”, IEEE Transactions on Pattern Analysis and Machine Intelligence, 16(6):641-647, 1994.

Arthur, “Clinical Use of Intracardiac Impedance: Current Applications and Future Perspectives”, PACE, vol. 24:500-506, Apr. 2001.

Authorized officer Blaine R. Copenheaver, International Search Report/Written Opinion in PCT/US2012/020935 dated May 8, 2012, 30 pages.

Authorized officer Carl H. Layno, International Search Report and the Written Opinion in PCT/US07/70854 dated Sep. 12, 2008, 15 pages.

Authorized officer, Blaine R. Copenheaver, International Search Report and the Written Opinion in PCT/US2009/061277 dated Apr. 8, 2010, 13 pages.

Baan, Jan et al., “Continuous Measurement of Left Ventricular Volume In Animals and Humans by Conductance Catheter”, Circulation, 07(5):812-823, 1984.

Badics, “Real-Time Reconstruction of Endocardial Potential Maps in Non-Contact Cardiace Mapping”, International Journal for computation and Mathematics in Electrical Engineering (COMPEL), vol. 28, No. 4, 2009.

Ben-Haim et al., “Nonfluoroscopic, in Vivo Navigation and Mapping Technology”, Nature Medicine, 2(12)1393-1395, 1996.

Besl et al., “A Method for Registration of 3-D Shapes”, IEEE Transaction on Pattern Analysis and Machine Intelligence, 14(2):239-256, 1992.

Blomstrom-Lundqvist et al., “ACC/AHA/ESC Guidelines for the Management of Patients with Supraventricular Arrhythmias-Executive Summary”, Journal of the American College of Cardiology, 42(8):1493-1531, 2003.

Breithardt et al., “AHA Medical/Scientific Statement—Special Report: Standards for Analysis of Ventricular Late Potentials Using High-Resolution or Signal/Averaged Electrocardiography”, Circulation, 83(4):1481-1488, 1991.

Brooks et al., “Electrical Imaging of the Heart”, IEEE Signal Processing Magazine, pp. 24-42, 1997.

Caspi et al., “Stem Cell Research: Regenerating the Heart Using Human Embryonic Stem Cells—from Cell to Bedside”, IMAJ 8:208-214, 2006.

De Groot et al., “Three-Dimensional Catheter Positioning During Radiofrequency Ablation in Patients: First Application of a Real-Time Position Management System”, Journal of Cardiovascular Electrophysiology, 11:1183-1192, 2000.

Donahue et al., “Focal Modification of Electrical Conduction in the Heart by Viral Gene Transfer”, Nature Medicine, 6(12):1395-1398, 2000.

Dong et al., “Integrated Electroanatomic Mapping With Three-Dimensional Computed Tomographic Images for Real-Time Guided Ablations”, Circulation 113:186-194, 2006.

Durrer et al., “Total Excitation of the Isolated Human Heart”, Circulation, XL1:899-912, 1970.

(56) References Cited

OTHER PUBLICATIONS

Ector, Joris et al., "Cardiac Three-Dimensional Magnetic Resonance Imaging and Fluoroscopy Merging", Circulation, 112:3769-3776, 2005.
Friedman, "Catheter Cryoablation of Cardiac Arrhythmias", Current Opinion in Cardiology, 20:48-54, 2005.
Friedman, "Novel Mapping Techniques for Cardiac Electrophysiology", Heart, 87:575-582, 2002.
Gepstein et al., "A Novel Method for Nonfluoroscopic Catheter-Based Electroanatomical Mapping of the Heart", Circulation 95:1611-1622, 1997.
Huang, Yi-Chih et al., "Development of a Third Generation Intraventricular Impedance Imaging (Iii) System Evaluation of Hardware Design", Engineering in Medicine and Biology Society, Proceedings of the 19th Annual Internal Conference of the IEEE/EMBS, 6:2442-2444 Oct. 30-Nov. 2, 1997.
International Preliminary Report on Patentability, PCT/US2012/020935, dated Jul. 25, 2013, 24 pages.
International Search Report and the Written Opinion in PCT/US08/52385 dated Aug. 8, 2008, 11 pages.
Jain et al., "Cell Therapy Attenuates Deleterious Ventricular Remodeling and Improves Cardiac Performance after Myocardial Infarction", Circulation, 103:1920-1927, 2001.
Jalife, "Rotors and Spiral Waves in Atrial Fibrillation", Journal of Cardiovascular Electrophysiology, 14:776-730, 2003.
Jane et al., Alignment Methods for Averaging of High-Resolution Cardiac Signals: A Comparative Study of Performance, IEEE Transaction on Biomedical Engineering, 38(6):571-579, 1991.
Jia et al., "Electrophysiologic Endocardial Mapping from a Noncontact Nonexpandable Catheter: A Validation Study of a Geometry-Based Concept". Journal of Cardiovascular Electrophysiology, 11:1238-1251, 2000.
Ju et al., "Mean value coordinates for closed triangular meshes," ACM Trans, Graph. 24(3):561-566 (2005).
Kikuchi et al., "Targeted Modification of Atrial Electrophysiology by Homogeneous Transmural Artial Gene Transfer", Circulation, 111:264-270, 2005.
Kistler et al., "Validation of Three-Dimensional Cardiac Image Integration: Use of Integrated CT Image into Electroanatomic Mapping System to Performa Catheter Ablation of Atrial Fibrillation", Journal of Cardiovascular Electrophysiology, 17:341-348, 2006.
Kun, Stevan et al., "Conductance Volumetric Model of an Eccentrically Positioned Catheter within a Three-Compartment Ellipsoidal Ventricle", U, IEEE Transactions on Jun. 1993, 40(6); 589-592.
Laciar et al., "Improved Alignment Method for Noisy High-Resolution ECG and Holter Records Using Multiscale Cross-Correlation", IEEE Transactions on Biomedical Engineering, 50(3):344-353, 2003.
Liu et al., "Endocardial Potential Mapping from a Noncontact Nonexpandable Catheter: A Feasibility Study", Annals of Biomedical Engineering, 26:994-1009, 1998.
Lorensen et al., "Marching Cubes: A High Resolution 3D Surface Construction Algorithm", Computer Graphics 21(4):163-169, Jul. 1987.
Makela et al., "A Review of Cardiac Image Registration Methods", IEEE Transaction on Medical Imaging, 21(9):1011-1021, 2002.
Malladi, R. et al., "A Geometric Approach to Segmentation and Analysis of 3D Medical Images", Mathematical Methods in Biomedical Image Analysis, Proceedings of the Workshop on, Jun. 21-22, 1996, pp. 244-252.
Mangan, Alan et al., "Partitioning 3D Surface Meshes Using Watershed Segmentation", IEEE Transactions on Visualization and Computer Graphics, 5(4):308-321, 1999.
McLeish et al., "A Study of the Motion and Deformation of the Heart Due to Respiration," IEEE Transactions on Medical Imaging, 21(9):1142-1150 (2002).
Meininger et al., "Initial Experience with a Novel Focused Ultrasound Ablation System for Ring Ablation Outside the Pulmonary Vein", Journal of Interventional Cardiac Electrophysiology, 8:141-148, 2003.
Merrill, Daniel R. et al., "Electrical stimulation of excitable tissue: design of efficacious and safe protocols", Journal of Neuroscience Methods, 141:171-198, 2005.
Miller, "Editor's Forum—Application of Registration for Ablation: A Marriage of Technologies", Journal of Interventional Cardiac Electrophysiology, 11:87-89, 2004.
Nademanee et al., "A New Approach for Catheter Ablation of Atrial Fibrillation: Mapping of the Electrophysiologic Substrate", Journal of the American College of Cardiology, 43(11):2044-2053, 2004.
Noseworthy et al., "The Impact of Respiration on Left Atrial and Pulmonary Venous Anatomy: Implications for Image-Guided Intervention", Heart Rhythm, 2:1173-1178, 2005.
Pappone et al., "Robotic Magnetic Navigation for Atrial Fibrillation Ablation", Journal of the American College of Cardiology, 47(7): 1390-1400, 2006.
Paragios, "A Level Set Approach for Shape-Driven Segmentation and Tracking of the Left Ventricle", IEEE Transactions on Medical Imaging, 22(6):773-776, 2003.
Persson et al., "A Simple Mesh Generator in MATLAB", SIAM Review, 46(2):329-345, 2004.
Pham, Dzung, et al., "Current Methods in Medical Image Segmentation", Annu. Rev. Biorned. Eng., 02:315-337, 2000.
Rao et al., "Novel Noncontact Catheter System for Endocardial Electrical and Anatomical Imaging", Annals of Biomedical Engineering, 32(4):573-584, 2004.
Reddy et al., "Use of a Diode Laser Balloon Ablation Catheter to Generate Circumferential Pulmonary Venous Lesions in an Open-Thoracotomy Caprine Model", PACE, 27:52-57, 2004.
Cheney, Margaret, et al. "Electrical Impedance Tomography." Society for Industrial and Applied Mathematics, Review, 41(1):85-101, Mar. 1999.
Geddes, L.A. et al., "Criteria for the Selection of Materials for Implanted Electrodes", Annals of Biomedical Engineering, vol. 31, pp. 879-890 (2003).
Haug. E. J. et al.: Design Sensitivity Analysis of Structural Systems, Mathematics in Science and Engineering, vol. 177 (1986).
International Search Report and Written Opinion issued in PCT/US2009/036099, dated Apr. 28, 2009, 21 pages.
International Search Report and Written Opinion issued in PCT/US2009/061277, dated Apr. 8, 2010, 12 pages.
International Search Report and Written Opinion issued in PCT/US2016/053627, dated Feb. 14, 2017, 17 pages.
Invitation to Pay Additional Fees, and, Where Applicable, Protest Fee issued in PCT/US2016/053627, dated Dec. 21, 2016, 8 pages.
Kukiik et al., "The reconstruction, from a set of points, and analysis of the interior surface of the heart chamber", Physiol. Meas. 25:617-627, 2004.
L. Piegl, W. Tiller: The NURBS Book, 2nd Edition, Springer (1997).
Persson, Per-Olof. "Mesh Generation for Implicit Geometries." Massachusetts Institute of Technology, Thesis, Feb. 2005, 126 pages.
Extended International Search Report issued in European application 12733844.0, dated Jun. 26, 2017, 9 pages.
Extended International Search Report issued in European Application 12734224.4, dated Jun. 27, 2017, 10 pages.
Kriebel et al., "Noncontact Mapping and Radiofrequency Catheter Ablation of Fast and Hernodynarnically Unstable Ventricular Tachycardia After Surgical Repair of Tetralogy of Fallot", Journal of the American College of Cardiology, Elsevier, New York, NY, vol. 50, No, 22, Nov. 13, 2007, pp. 2162-2168.
Martin K. Stiles et al., "The Effect of Electrogram Duration on Quantification of Complex Fractionated Atrial Electrograms and Dominant Frequency", Journal of Cardiovascular Electrophysiology, vol. 19, No, 3, Mar. 1, 2008, pp. 252-258.
Wazni et al., "Atrial Arrhythmias After Surgical Maze", Journal of the American College of Cardiology, Elsevier, New York, NY, vol. 48, No. 7, Oct. 3, 2006, pp. 1405-1409.

ELECTROANATOMICAL MAPPING

CROSS-REFERENCE TO RELATED APPLICATION

This application is a continuation of U.S. application Ser. No. 14/809,858, filed Jul. 27, 2015, which is a continuation of U.S. application Ser. No. 13/717,856, filed Dec. 18, 2012, now U.S. Pat. No. 9,107,599, which is a continuation of U.S. application Ser. No. 13/182,830, filed Jul. 14, 2011, now U.S. Pat. No. 8,428,700, which claims priority to Provisional Application No. 61/432,404, filed Jan. 13, 2011, all of which are herein incorporated by reference in their entirety.

TECHNICAL FIELD

This invention relates to the determination and representation of physiological information relating to a heart surface such as electroanatomical mapping and annotation.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Conventional 3D mapping techniques include contact mapping and non-contact mapping. In contact mapping techniques one or more catheters are advanced into the heart. Physiological signals resulting from the electrical activity of the heart are acquired with one or more electrodes located at the catheter distal tip after determining that the tip is in stable and steady contact with the endocardium surface of a particular heart chamber. Location and electrical activity is usually measured sequentially on a point-by-point basis at about 50 to 200 points on the internal surface of the heart to construct an electro-anatomical depiction of the heart. The generated map may then serve as the basis for deciding on a therapeutic course of action, for example, tissue ablation, to alter the propagation of the heart's electrical activity and to restore normal heart rhythm. On the other hand, in non-contact-based mapping systems a multiple electrode catheter is percutaneously placed in the heart chamber of interest. Once in the chamber, the catheter is deployed to assume a 3D shape. Using the signals detected by the non-contact electrodes and information on chamber anatomy and relative electrode location, the system provides physiological information regarding the endocardium of the heart chamber.

SUMMARY

In some aspects, a method for providing information about a patient's heart includes measuring signals from one or more electrodes at multiple positions in the heart cavity in response to electrical activity in the patient's heart cavity over multiple heart beat cycles. The method also includes generating the electroanatomical representation of a patient's heart based on the signals measured at the electrodes and information about the positions of the electrodes. The method also includes generating, by a computer, annotation information for the measured signals by applying one or more operators to the measured signals. The method also includes conveying at least some of the annotation information to a user.

Embodiments can include one or more of the following.

The annotation information can include information related to activation time.

The annotation information can include information related to double activation.

The annotation information can include information related to fractionation.

The annotation information can include information related to voltage amplitude.

The annotation information can include information related to spectral content.

Generating the annotation can include identifying at least one of regions of the heart having double deflections, regions of the heart having multiple deflections, regions of the heart having fractionation, and regions of the heart having no activation.

Generating the annotation information can include applying an algorithm to the measured signals to detect double deflections and conveying at least some of the annotation information can include displaying an indicator on an electroanatomical representation of a patient's heart identifying regions of double deflections.

Generating the annotation information can include applying an algorithm to the measured signals to detect fractionation and conveying at least some of the annotation information can include displaying an indicator on an electroanatomical representation of a patient's heart identifying regions of fractionation.

Generating the annotation information can include applying an algorithm to the measured signals to detect no activation and conveying at least some of the annotation information can include displaying an indicator on an electroanatomical representation of a patient's heart identifying regions of no activation.

The method can also include receiving from an operator a change to the automatically generated annotation information for a specified measured signal and modifying, by the computer, annotation information for one or more additional measured signals based on the change.

Modifying the annotation information can include automatically modifying the annotation information by the computer. Adjusting the annotation information for one or more additional measured signals can include automatically adjusting annotation information for one or more additional measured signals in spatial proximity to the specified measured signal.

The measured signals in spatial proximity to the specified measured signal can include signals at positions within a set distance to the specified measured signal.

The signals measured at the one or more electrodes can include electrograms.

The method can also include receiving from an operator a change to the automatically generated annotation information for a specified electrogram and automatically, by the computer, adjusting the annotation information for other electrograms based on the operator change to the annotation information for the specified electrogram.

The method can also include receiving from an operator a change to an activation time for a specified measured signal and automatically, by the computer, adjusting activation times for one or more additional measured signals based on the operator change.

At least some of the signals measured at the one or more electrodes can include electrograms.

Generating the annotation information can include generating annotation information based on a specified electrogram and spatially neighboring electrograms.

Spatially neighboring electrograms can include electrograms within a predefined distance.

Generating the annotation information can include for electrograms including multiple deflections, selecting a deflection of the multiple deflections based on timing information for the multiple deflections and timing information for deflections in spatially neighboring electrograms and using the selected deflection to determine the annotation information.

Spatially neighboring electrograms can include electrograms within a set distance to the specified measured signal.

Generating the annotation information can include generating annotation information for a specific location of the endocardium based on the signals measured at an electrode location corresponding to the specific location and signals measured at one or more additional electrodes at locations in spatial proximity to the electrode location corresponding to the specific location.

The one or more additional electrodes at locations in spatial proximity to the specific location can include one or more additional electrodes within a set distance to the specified measured signal.

Generating the annotation information can include using spatial information about the positions at which the signals were measured to determine local timing information.

Generating the annotation information can include using signals measured by multiple, different electrodes to determine local timing information.

The one or more electrodes can include one or more electrodes on an intracardiac catheter.

Conveying at least some of the annotation information to the user can include displaying an electroanatomical representation of a patient's heart and at least some of the annotation information.

The method can also include inserting a catheter comprising the one or more electrodes into the heart cavity and moving the catheter to each of multiple, different positions in the heart cavity.

The method can also include synchronizing the signals measured at the multiple positions with one another according to a heart beat cycle.

The method can also include generating the electroanatomical representation of the patient's heart by determining physiological information at multiple locations of the endocardium surface based on the measured signals at the multiple positions by processing the synchronized signals.

Processing the synchronized signals can include processing the synchronized signals as though they were obtained at one time.

The method can also include generating an electroanatomical representation of the patient's heart.

The method can also include generating the electroanatomical representation of the patient's heart comprises determining physiological information by processing the measured signals based at least in part on a mathematical operator approximating Laplace's equation.

The method can also include displaying at least a portion of the electroanatomical representation of a patient's heart.

The method can also include using the electroanatomical representation of a patient's heart to guide treatment of the heart cavity.

The treatment can include ablation of one or more selected regions of the heart.

The treatment can include cell therapy, gene therapy, or the application of other biological agents.

Generating the electroanatomical representation of the patient's heart can include determining physiological information at multiple locations of the endocardium surface by applying a transformation function to the signals, wherein the transformation function relates signals measured from at least some of the different positions in the heart cavity to the physiological information at the multiple locations of the endocardium surface.

The determination of the physiological information at the multiple locations of the endocardium surface further can include determining the transformation function by calculating a forward transformation for relating the physiological information at the multiple locations of the endocardium surface to the signals measured for the different positions of the catheter in the heart cavity and inverting the forward transformation.

The inverting can include reformulating an underdetermined matrix inversion by regularization.

The inverting can include a least squares minimization.

The method can also include selecting a subset of less than all of the signals and generating an electroanatomical representation of the patient's heart based on the selected subset of less than all of the signals.

Generating the electroanatomical representation of the patient's heart can include generating the electroanatomical representation of the patient's heart based on the signals measured at the electrodes and information about the positions of the electrodes with respect to the endocardium surface.

In some aspects, a system for providing information about patient's heart includes one or more electrodes for measuring signals at multiple positions in the heart cavity in response to electrical activity in the patient's heart cavity over multiple heart beat cycles. The system also includes an electronic processor coupled to the one or more electrodes. The electronic processor is configured to generate an electroanatomical representation of the patient's heart based on the signals measured at the electrodes and information about the positions of the electrodes, generate annotation information for the measured signals by applying one or more operators to the measured signals, and convey at least some of the annotation information to a user.

Embodiments can include one or more of the following.

The annotation information can include information related to activation time.

The annotation information can include information related to double activation.

The annotation information can include information related to fractionation. The annotation information can include information related to voltage amplitude.

The annotation information can include information related to spectral content.

The electronic processor can configured to generate the annotation information by identifying at least one of regions of the heart having double deflections, regions of the heart having multiple deflections, regions of the heart having fractionation, and regions of the heart having no activation.

The electronic processor can be configured to generate the annotation information by applying an algorithm to the measured signals to detect double deflections and the electronic processor can be configured to convey at least some of the annotation information by displaying an indicator on an electroanatomical representation of a patient's heart identifying regions of double deflections.

The electronic processor can be configured to generate the annotation information by applying an algorithm to the measured signals to detect fractionation and the electronic processor can be configured to convey at least some of the annotation information by displaying an indicator on an electroanatomical representation of a patient's heart identifying regions of fractionation.

The electronic processor can be configured to generate the annotation information by applying an algorithm to the measured signals to detect no activation and the electronic processor can be configured to convey at least some of the annotation information by displaying an indicator on an electroanatomical representation of a patient's heart identifying regions of no activation.

The electronic processor can be further configured to receive from an operator a change to the automatically generated annotation information for a specified measured signal and modify annotation information for one or more additional measured signals based on the change.

The electronic processor can be configured to modify the annotation information by automatically modifying the annotation information.

The electronic processor can be configured to adjust the annotation information for one or more additional measured signals by automatically adjusting annotation information for one or more additional measured signals in spatial proximity to the specified measured signal.

The measured signals in spatial proximity to the specified measured signal can include signals at positions within a radius of influence to the specified measured signal.

The signals measured at the one or more electrodes can be electrograms.

The electronic processor can be further configured to receive from an operator a change to the automatically generated annotation information for a specified electrogram and automatically adjust the annotation information for other electrograms based on the operator change to the annotation information for the specified electrogram.

The electronic processor can be further configured to receive from an operator a change to an activation time for a specified measured signal and automatically adjust activation times for one or more additional measured signals based on the operator change.

At least some of the signals measured at the one or more electrodes comprise electrograms.

The electronic processor can be configured to generate the annotation information by generating annotation information based on a specified electrogram and spatially neighboring electrograms.

Spatially neighboring electrograms can be electrograms within a set distance to the specified measured signal.

The electronic processor can be configured to generate for electrograms including multiple deflections, selecting a deflection of the multiple deflections based on timing information for the multiple deflections and timing information for deflections in spatially neighboring electrograms and using the selected deflection to determine the annotation information.

Spatially neighboring electrograms can include electrograms within a set distance to the specified measured signal.

The electronic processor can be configured to generate the annotation information by generating annotation information for a specific location of the endocardium based on the signals measured at an electrode location corresponding to the specific location and signals measured at one or more additional electrodes at locations in spatial proximity to the electrode location corresponding to the specific location.

The one or more additional electrodes at locations in spatial proximity to the specific location can include one or more additional electrodes within a set distance to the specified measured signal.

The electronic processor can be configured to generate the annotation information by using spatial information about the positions at which the signals were measured to determine local timing information.

The electronic processor can be configured to generate the annotation information using signals measured by multiple, different electrodes to determine local timing information.

The one or more electrodes can be one or more electrodes on an intracardiac catheter.

The electronic processor is further configured to comprising synchronize the signals measured at the multiple positions with one another according to a heart beat cycle.

The electronic processor can be configured to generate an electroanatomical representation of the patient's heart by determining physiological information at multiple locations of the endocardium surface based on the measured signals at the multiple positions by processing the synchronized signals.

The electronic processor can be configured to generate the electroanatomical representation of the patient's heart by determining physiological information by processing the measured signals based at least in part on a mathematical operator approximating Laplace's equation.

The electronic processor can be further configured to display at least a portion of the electroanatomical representation of a patient's heart.

The electronic processor can be configured to generate the electroanatomical representation of the patient's heart by determining physiological information at multiple locations of the endocardium surface by applying a transformation function to the signals, wherein the transformation function relates signals measured from at least some of the different positions in the heart cavity to the physiological information at the multiple locations of the endocardium surface.

The determination of the physiological information at the multiple locations of the endocardium surface can include determining the transformation function by calculating a forward transformation for relating the physiological information at the multiple locations of the endocardium surface to the signals measured for the different positions of the catheter in the heart cavity and inverting the forward transformation.

The electronic processor can be further configured to select a subset of less than all of the signals and generating an electroanatomical representation of the patient's heart based on the selected subset of less than all of the signals.

In some aspects, a method for providing information about a patient's heart can include measuring signals from one or more electrodes at multiple positions in the heart cavity in response to electrical activity in the patient's heart cavity over multiple heart beat cycles. The method can also include generating, by a computer, annotation information for the measured signals by applying one or more operators to the measured signals to identify at least one of regions of the heart having double deflections, regions of the heart having multiple deflections, regions of the heart having fractionation, regions of the heart having double activation, and regions of the heart having no activation. The method can also include generating, by the computer, an electroanatomical representation of the patient's heart that includes at least some of the annotation information.

Embodiments can include one or more of the following.

The annotation information can include information related to activation time.

The annotation information can include information related to double activation.

The annotation information can include information related to fractionation.

The annotation information can include information related to voltage amplitude.

The annotation information can include information related to spectral content.

Generating the annotation information can include applying an algorithm to the measured signals to detect double deflections and generating the electroanatomical representation can include identifying regions of double deflections.

Generating the annotation information can include applying an algorithm to the measured signals to detect fractionation and generating the electroanatomical representation can include identifying regions of fractionation.

Generating the annotation information can include applying an algorithm to the measured signals to detect no activation and generating the electroanatomical representation can include identifying regions of no activation.

The method can also include receiving from an operator a change to the annotation information for a specified measured signal and modifying, by the computer, annotation information for one or more additional measured signals based on the change.

Modifying the annotation information for one or more additional measured signals can include automatically adjusting annotation information for one or more additional measured signals in spatial proximity to the specified measured signal.

Generating the annotation information can include generating annotation information based on a specified electrogram and spatially or temporally neighboring electrograms.

Generating the annotation information can include generating annotation information for a specific location of the endocardium based on the signals measured at an electrode location corresponding to the specific location and signals measured at one or more additional electrodes at locations in spatial proximity to the electrode location corresponding to the specific location.

Generating the annotation information can include generating annotation information for a specific location of the endocardium based on the signals measured at an electrode location corresponding to the specific beat and signals measured at one or more previous beats at the same electrode.

The one or more electrodes can include one or more electrodes on an intracardiac catheter.

The method can also include inserting a catheter comprising the one or more electrodes into the heart cavity and moving the catheter to each of multiple, different positions in the heart cavity.

The method can also include synchronizing the signals measured at the multiple positions with one another according to a heart beat cycle.

The method can also include using the electroanatomical representation of a patient's heart to guide treatment of the heart cavity.

The treatment can include ablation of one or more selected regions of the heart.

The treatment can include cell therapy, gene therapy, or the application of other biological agents.

The method can also include selecting a subset of less than all of the signals and generating an electroanatomical representation of the patient's heart based on the selected subset of less than all of the signals.

In some aspects, a method for providing information about a patient's heart can include measuring signals from one or more electrodes at multiple positions in the heart cavity in response to electrical activity in the patient's heart cavity over multiple heart beat cycles. The method can also include generating, by a computer, annotation information for the measured signals by applying one or more operators on a specified measured signal and spatially or temporally neighboring measured signals. The method can also include generating, by the computer, an electroanatomical representation of the patient's heart that includes at least some of the annotation information.

Embodiments can include one or more of the following.

The annotation information can include information related to activation time.

The annotation information can include information related to double activation.

The annotation information can include information related to fractionation.

The annotation information can include information related to voltage amplitude.

The annotation information can include information related to spectral content.

Generating the annotation information can include applying one or more operators to the measured signals to identify at least one of regions of the heart having double deflections, regions of the heart having multiple deflections, regions of the heart having fractionation, regions of the heart having double activation, and regions of the heart having no activation.

The method can also include receiving from an operator a change to the annotation information for a specified measured signal and modifying, by the computer, annotation information for one or more additional measured signals based on the change.

Modifying the annotation information can include automatically modifying the annotation information by the computer.

Modifying the annotation information for one or more additional measured signals can include automatically adjusting annotation information for one or more additional measured signals in spatial proximity to the specified measured signal.

The measured signals in spatial proximity to the specified measured signal can be signals at positions within a set distance to the specified measured signal.

The signals measured at the one or more electrodes can be electrograms.

The method can also include receiving from an operator a change to the annotation information for a specified electrogram and automatically, by the computer, adjusting the annotation information for other electrograms based on the operator change to the annotation information for the specified electrogram.

Spatially neighboring electrograms can include electrograms within a predefined distance.

Generating the annotation information can include for electrograms including multiple deflections, selecting a deflection of the multiple deflections based on timing information for the multiple deflections and timing information for deflections in spatially neighboring electrograms and using the selected deflection to determine the annotation information.

Generating the annotation information can include generating annotation information for a specific location of the endocardium based on the signals measured at an electrode location corresponding to the specific location and signals measured at one or more additional electrodes at locations in spatial proximity to the electrode location corresponding to the specific location.

The one or more additional electrodes at locations in spatial proximity to the specific location can include one or more additional electrodes within a predefined distance to the specific location.

Generating the annotation information can include generating annotation information for a specific location of the endocardium based on the signals measured at an electrode location corresponding to the specific beat and signals measured at one or more previous beats at the same electrode.

Generating the annotation information can include using spatial information about the positions at which the signals were measured to determine local timing information.

The one or more electrodes can be one or more electrodes on an intracardiac catheter.

The method can also include using the electroanatomical representation of a patient's heart to guide treatment of the heart cavity.

The method can also include selecting a subset of less than all of the signals and generating an electroanatomical representation of the patient's heart based on the selected subset of less than all of the signals.

In some aspects system for providing information about patient's heart includes one or more electrodes for measuring signals at multiple positions in the heart cavity in response to electrical activity in the patient's heart cavity over multiple heart beat cycles. The system also includes an electronic processor coupled to the one or more electrodes configured to generate annotation information for the measured signals by applying one or more operators to the measured signals to identify at least one of regions of the heart having double deflections, regions of the heart having multiple deflections, regions of the heart having fractionation, regions of the heart having double activation, and regions of the heart having no activation and generate by the computer, an electroanatomical representation of the patient's heart that includes at least some of the annotation information.

Embodiments can include one or more of the following.

The electronic processor can be configured to generate the annotation information by applying an algorithm to the measured signals to detect double deflections and the electronic processor can be configured to generate the electroanatomical representation by identifying regions of double deflections.

The electronic processor can be configured to generate the annotation information by applying an algorithm to the measured signals to detect fractionation and the electronic processor can be configured to generate the electroanatomical representation by identifying regions of fractionation.

The electronic processor can be configured to generate the annotation information by applying an algorithm to the measured signals to detect no activation and the electronic processor can be configured to generate the electroanatomical representation by identifying regions of no activation.

The electronic processor can be further configured to receive from an operator a change to the automatically generated annotation information for a specified measured signal and modify annotation information for one or more additional measured signals based on the change.

The electronic processor can be configured to adjust the annotation information for one or more additional measured signals by automatically adjusting annotation information for one or more additional measured signals in spatial proximity to the specified measured signal.

The measured signals in spatial proximity to the specified measured signal can be signals at positions within a set distance to the specified measured signal.

The electronic processor can be further configured to receive from an operator a change to an activation time for a specified measured signal and automatically adjust activation times for one or more additional measured signals based on the operator change.

At least some of the signals measured at the one or more electrodes can be electrograms.

The electronic processor can be configured to generate the annotation information by generating annotation information based on a specified electrogram and spatially or temporally neighboring electrograms.

Spatially neighboring electrograms can be electrograms within a set distance to the specified measured signal.

The electronic processor can be configured to generate the annotation information by for electrograms including multiple deflections, selecting a deflection of the multiple deflections based on timing information for the multiple deflections and timing information for deflections in spatially neighboring electrograms and using the selected deflection to determine the annotation information.

Spatially neighboring electrograms comprise electrograms within a set distance to the specified measured signal.

The electronic processor can be configured to generate the annotation information by generating annotation information for a specific location of the endocardium based on the signals measured at an electrode location corresponding to the specific location and signals measured at one or more additional electrodes at locations in spatial proximity to the electrode location corresponding to the specific location.

The electronic processor can be configured to generate the annotation information by generating annotation information for a specific location of the endocardium based on the signals measured at an electrode location corresponding to the specific beat and signals measured at one or more previous beats at the same electrode.

The one or more electrodes can be one or more electrodes on an intracardiac catheter.

In some aspects, a system for providing information about patient's heart can include one or more electrodes for measuring signals at multiple positions in the heart cavity in response to electrical activity in the patient's heart cavity over multiple heart beat cycles. The system can also include an electronic processor coupled to the one or more electrodes, wherein the electronic processor is configured to generate annotation information for the measured signals by applying one or more operators a specified measured signal and spatially or temporally neighboring measured signals and generate an electroanatomical representation of the patient's heart that includes at least some of the annotation information.

Embodiments can include one or more of the following.

The electronic processor can be further configured to generating the annotation information by applying one or more operators to the measured signals to identify at least one of regions of the heart having double deflections, regions of the heart having multiple deflections, regions of the heart having fractionation, regions of the heart having double activation, and regions of the heart having no activation.

The electronic processor can be further configured to receive from an operator a change to the annotation information for a specified measured signal and modify annotation information for one or more additional measured signals based on the change.

The electronic processor can be further configured to adjust the annotation information for one or more additional measured signals by automatically adjusting annotation information for one or more additional measured signals in spatial proximity to the specified measured signal.

The measured signals in spatial proximity to the specified measured signal can be signals at positions within a set distance to the specified measured signal.

The signals measured at the one or more electrodes can be electrograms.

The electronic processor can be further configured to receive from an operator a change to the annotation information for a specified electrogram and automatically adjust the annotation information for other electrograms based on the operator change to the annotation information for the specified electrogram.

Spatially neighboring electrograms can be electrograms within a predefined distance.

The electronic processor can be further configured to generate the annotation information by for electrograms including multiple deflections, selecting a deflection of the multiple deflections based on timing information for the multiple deflections and timing information for deflections in spatially neighboring electrograms and using the selected deflection to determine the annotation information.

The electronic processor can be further configured to generate the annotation information by generating annotation information for a specific location of the endocardium based on the signals measured at an electrode location corresponding to the specific location and signals measured at one or more additional electrodes at locations in spatial proximity to the electrode location corresponding to the specific location.

The one or more additional electrodes at locations in spatial proximity to the specific location can be one or more additional electrodes within a predefined distance to the specific location.

The electronic processor can be further configured to generate the annotation information by generating annotation information for a specific location of the endocardium based on the signals measured at an electrode location corresponding to the specific beat and signals measured at one or more previous beats at the same electrode.

The electronic processor can be further configured to generate the annotation information using spatial information about the positions at which the signals were measured to determine local timing information.

The one or more electrodes can be one or more electrodes on an intracardiac catheter.

In some aspects, a method for providing information about a patient's heart can include measuring signals from one or more electrodes at multiple positions in the heart cavity in response to electrical activity in the patient's heart cavity over multiple heart beat cycles, generating, by a computer, annotation information for the measured signals by applying one or more operators to the measured signals, and receiving from an operator a change to the annotation information for a specified measured signal, modifying, by the computer, annotation information for one or more additional measured signals based on the change, and generating, by the computer, an electroanatomical representation of the patient's heart that includes at least some of the annotation information and at least some of the modified annotation information.

Embodiments can include one or more of the following.

Generating the annotation information can include identifying at least one of regions of the heart having double deflections, regions of the heart having multiple deflections, regions of the heart having fractionation, regions of the heart having double activation, and regions of the heart having no activation.

Modifying the annotation information for one or more additional measured signals can include automatically adjusting annotation information for one or more additional measured signals in spatial proximity to the specified measured signal.

Modifying the annotation information for one or more additional measured signals can include automatically adjusting annotation information for one or more additional measured signals in temporal proximity to the specified measured signal.

Generating the annotation information can include generating annotation information based on a specified electrogram and spatially or temporally neighboring electrograms.

The one or more electrodes can be one or more electrodes on an intracardiac catheter.

The method can also include using the electroanatomical representation of a patient's heart to guide treatment of the heart cavity.

In some aspects, a method for providing information about an electroanatomical representation of a patient's heart, the method includes measuring signals at one or more electrodes at multiple positions in the patient's heart cavity over a time period including multiple heart beat cycles, at least some of the signals being in response to electrical activity in the patient's heart cavity. The method also includes applying an algorithm to one or more specific signals of the measured signals to determine a triggering event in the specific signal. The method also includes synchronizing, by the computer, the signals measured at the one or more electrodes with one another according to a heart beat cycle based on the triggering event and generating, by the computer, the electroanatomical representation of the patient's heart based on the synchronized measured signals and positions of the catheter electrodes.

Embodiments can include one or more of the following.

Applying the algorithm to the specific signal to determine the triggering event can include selecting portions of the specific signal to process to determine the triggering event based on a second, different signal of the measured signals.

Selecting portions of the specific signal can include selecting portions of the specific signal to exclude from processing.

Selecting portions of the specific signal can include selecting portions of the specific signal to include in processing.

The method can also include processing the second signal to determine an event corresponding in time to a potential false triggering event in the specific signal and selecting portions of the specific signal to process to determine the triggering event can include selecting a portion of the specific signal that excludes the time period including the potential false triggering event.

Applying the algorithm to the one or more specific signals signal to determine the triggering event can include processing the specific signal using a sliding window integration to generate a reference signal and analyzing the reference signal to determine the triggering event.

Applying the algorithm to the one or more specific signals to determine the triggering event can include processing the specific signal to generate a representation of instantaneous energy and analyzing the representation of instantaneous energy to determine the triggering event.

Applying the algorithm to the one or more specific signals to determine the triggering event can include applying an algorithm to generate a representation of the signal having reduced jitter and analyzing the representation of the signal having reduced jitter to determine the triggering event.

Applying the algorithm to the one or more specific signals to determine the triggering event can include applying an algorithm to integrate the signal over a window and apply an operator to ensure the result of the algorithm is positive.

The one or more electrodes can include one or more electrodes on an intracardiac catheter.

The method can also include generating, by the computer, annotation information for the measured signals by applying one or more algorithms to the measured signals.

The method can also include conveying at least some of the annotation information to the user.

The method can also include inserting a catheter comprising the one or more electrodes into the heart cavity and moving the catheter to each of multiple, different positions in the heart cavity.

Generating the electroanatomical representation of the patient's heart can include determining physiological information at multiple locations of the endocardium surface based on the measured signals at the multiple positions by processing the synchronized signals.

Processing the synchronized signals can include processing the synchronized signals as though they were obtained at one time.

Generating the electroanatomical representation of the patient's heart can include determining physiological information by processing the measured signals based at least in part on a mathematical operator approximating Laplace's equation.

The method can also include displaying at least a portion of the electroanatomical representation of a patient's heart.

The method can also include using the electroanatomical representation of a patient's heart to guide treatment of the heart cavity.

The treatment can include ablation of one or more selected regions of the heart.

The treatment can include cell therapy, gene therapy, or the application of other biological agents.

Generating the electroanatomical representation of the patient's heart can include determining physiological information at multiple locations of the endocardium surface by applying a transformation function to the signals, wherein the transformation function relates signals measured from at least some of the different positions in the heart cavity to the physiological information at the multiple locations of the endocardium surface.

The determination of the physiological information at the multiple locations of the endocardium surface can include determining the transformation function by calculating a forward transformation for relating the physiological information at the multiple locations of the endocardium surface to the signals measured for the different positions of the catheter in the heart cavity and inverting the forward transformation.

The inverting can include reformulating an underdetermined matrix inversion by regularization.

The inverting further can include a least squares minimization.

The method can also include selecting a subset of less than all of the signals. Generating the electroanatomical representation of the patient's heart can include generating the electroanatomical representation of the patient's heart based on the selected subset of less than all of the signals.

In some aspects, a system for providing information about an electroanatomical representation of a patient's heart includes one or more electrodes for measuring signals at multiple positions in the patient's heart cavity over a time period including multiple heart beat cycles, at least some of the signals being in response to electrical activity in the patient's heart cavity. The system also includes an electronic processor coupled to the one or more electrodes, wherein the electronic processor is configured to apply an algorithm to one or more specific signals of the measured signals to determine a triggering event in the specific signal, synchronize the signals measured at the one or more electrodes with one another according to a heart beat cycle based on the triggering event, and generate the electroanatomical representation of the patient's heart based on the synchronized measured signals and positions of the catheter electrodes.

The electronic processor can be configured to apply the algorithm to the specific signal to determine the triggering event by selecting portions of the specific signal to process to determine the triggering event based on a second, different signal of the measured signals.

The electronic processor can be configured to select portions of the specific signal by selecting portions of the specific signal to exclude from processing.

The electronic processor can be configured to select portions of the specific signal by selecting portions of the specific signal to include in processing.

The electronic processor can be further configured to process the second signal to determine an event corresponding in time to a potential false triggering event in the specific signal and select portions of the specific signal to process to determine the triggering event by selecting a portion of the specific signal that excludes the time period including the potential false triggering event.

The electronic processor can be configured to apply the algorithm to the one or more specific signals signal to determine the triggering event by processing the specific signal using a sliding window integration to generate a reference signal and analyzing the reference signal to determine the triggering event.

The electronic processor can be configured to apply the algorithm to the one or more specific signals to determine the triggering event by processing the specific signal to generate a representation of instantaneous energy and analyzing the representation of instantaneous energy to determine the triggering event.

The electronic processor can be configured to apply the algorithm to the one or more specific signals to determine the triggering event by applying an algorithm to generate a representation of the signal having reduced jitter and analyzing the representation of the signal having reduced jitter to determine the triggering event.

The electronic processor can be configured to apply the algorithm to the one or more specific signals to determine the triggering event by applying an algorithm to integrate the signal over a window and apply an operator to ensure the result of the algorithm is positive.

The one or more electrodes can be one or more electrodes on an intracardiac catheter.

The electronic processor is further configured to comprising synchronize the signals measured at the multiple positions with one another according to a heart beat cycle.

The electronic processor can be configured to generate an electroanatomical representation of the patient's heart by determining physiological information at multiple locations of the endocardium surface based on the measured signals at the multiple positions by processing the synchronized signals.

The electronic processor can be configured to generate the electroanatomical representation of the patient's heart by determining physiological information by processing the measured signals based at least in part on a mathematical operator approximating Laplace's equation.

The electronic processor can be further configured to display at least a portion of the electroanatomical representation of a patient's heart.

The electronic processor can be configured to generate the electroanatomical representation of the patient's heart by determining physiological information at multiple locations of the endocardium surface by applying a transformation function to the signals, wherein the transformation function relates signals measured from at least some of the different positions in the heart cavity to the physiological information at the multiple locations of the endocardium surface.

The determination of the physiological information at the multiple locations of the endocardium surface can include determining the transformation function by calculating a forward transformation for relating the physiological information at the multiple locations of the endocardium surface to the signals measured for the different positions of the catheter in the heart cavity and inverting the forward transformation.

The electronic processor can be further configured to select a subset of less than all of the signals and generating an electroanatomical representation of the patient's heart based on the selected subset of less than all of the signals.

In some aspects, a method for providing information about an electroanatomical representation of a patient's heart includes measuring signals at one or more electrodes at multiple positions in the patient's heart cavity over a time period including multiple heart beat cycles, at least some of the signals being in response to electrical activity in the patient's heart. The method also includes processing, by a computer, the measured signals to determine a metric for each of the multiple heart beat cycles. The method also includes selecting, by the computer, a subset of the measured signals based on the metric associated with the heart beat cycle. The method also includes generating, by the computer, the electroanatomical representation of the patient's heart based on the selected subset of measured signals and positions of the electrodes.

Embodiments can include one or more of the following.

The metric can be a beat metric.

Measuring signals at the one or more electrodes can include measuring a signal indicative of tissue proximity.

The signal indicative of tissue proximity can be a force measurement.

The signal indicative of tissue proximity can be an impedance measurement.

Processing the signals to determine a the metric can include processing the signals to determine a measure of tissue proximity and selecting the subset of the signals based on the metric can include selecting the subset of signals based on the measure of tissue proximity.

Selecting the subset of signals indicative of the measure of tissue proximity can include selecting signals within about 3 mm of the endocardium surface.

Measuring signals at the one or more electrodes can include measuring a force on a catheter.

Measuring the signals can include measuring a signal indicative of contact with the endocardium surface, processing the signals to determine the metric can include processing the signal indicative of contact with the endocardium surface to determine a force measure, and selecting the subset of the signals based on the metric can include selecting the subset of signals having a force measure within a predetermined range.

Selecting the subset of signals having a force measure within a predetermined range can include selecting signals having a force measure above a first threshold and below a second threshold.

The metric can include an indication of contact with the endocardium surface.

The metric can include an indication of signal propagation and selecting, by the computer, the subset of the measured signals based on the metric can include selecting the subset of signals having metrics associated with normal signal propagation.

Measuring the signals can include measuring a first signal at a first electrode located in a first stable location and measuring a second signal at a second electrode located in a second stable location that is spaced apart from the first stable location, processing the measured signals can include determining a timing difference between activations in the first signal and the second signal, and selecting the subset of the measured signals can include selecting the subset of signals having a timing difference within a predetermined range.

Selecting the subset of the measured signals based on the metric can include selecting a subset of the measured signals for beats during which capture of a pacing signal occurred.

Measuring the signals can include measuring a pacing signal and measuring a second signal located in a stable location, and processing measured signals can include determining a timing difference between the pacing signal and activation in the second signal, the timing difference providing information associated with capture of the pacing signal by the patient's heart.

The metric can include an indication of ventrical activation and selecting, by the computer, the subset of the measured signals based on the metric can include selecting the subset of signals having metrics associated with the absence of ventricular activation.

The beat metric can include an indication of a far field signal and selecting, by the computer, the subset of the measured signals based on the metric can include selecting the subset of signals having metrics associated with the absence of the far field signal.

The metric can include an indication of electrogram consistency for spatially correlated signals, with the spatially correlated signals being measured at similar locations within the heart cavity, and selecting, by the computer, the subset of the measured signals based on the metric can include selecting the subset of signals having an electrogram consistency that is within a predetermined range.

Processing signals to determine a metric can include processing location information associated with the signals to determine signals measured at similar locations and processing the signals measured at similar locations to determine a measure of similarity between the signals measured at the similar locations and selecting, by the computer, the subset of the measured signals can include selecting the subset of signals based on the measure of similarity.

The metric can include an indication of electrogram consistency for temporally related signals, and selecting, by the computer, the subset of the measured signals based on the metric can include selecting the subset of signals having an electrogram consistency that is within a predetermined range.

Processing the signals to determine the metric can include processing the signals to determine a measure of similarity between at least two spatially correlated signals and selecting the subset of signals comprises selecting a subset of signals based on the determined measure of similarity between the at least two spatially correlated signals.

Processing the signals to determine the metric can include processing the signals to determine a measure of similarity between at least two temporally correlated signals and selecting the subset of signals comprises selecting a subset of signals based on the determined measure of similarity between the at least two temporally correlated signals.

The metric can be an indication of rapid changes in an electrogram.

Measuring the signals at one or more electrodes can include measuring the signals at one or more intracardiac electrodes in response to electrical activity in the patient's heart cavity.

The method can also include displaying the electroanatomical representation of the patient's heart.

The method can also include inserting a catheter comprising the one or more electrodes into the heart cavity and moving the catheter to each of multiple, different positions in the heart cavity.

The method can also include synchronizing the signals measured at the multiple positions with one another according to a heart beat cycle.

Generating the electroanatomical representation of the patient's heart can include determining physiological information at multiple locations of the endocardium surface based on the measured signals at the multiple positions by processing the synchronized signals.

Processing the synchronized signals can include processing the synchronized signals as though they were obtained at one time.

Generating the electroanatomical representation of the patient's heart can include determining physiological information by processing the measured signals based at least in part on a mathematical operator approximating Laplace's equation.

The method can also include displaying at least a portion of the electroanatomical representation of a patient's heart.

The method can also include using the electroanatomical representation of a patient's heart to guide treatment of the heart cavity.

The treatment can include ablation of one or more selected regions of the heart.

The treatment can include cell therapy, gene therapy, or the application of other biological agents.

Generating the electroanatomical representation of the patient's heart can include determining physiological information at multiple locations of the endocardium surface by applying a transformation function to the signals, wherein the transformation function relates signals measured from at least some of the different positions in the heart cavity to the physiological information at the multiple locations of the endocardium surface.

The determination of the physiological information at the multiple locations of the endocardium surface further can include determining the transformation function by calculating a forward transformation for relating the physiological information at the multiple locations of the endocardium surface to the signals measured for the different positions of the catheter in the heart cavity and inverting the forward transformation.

The inverting can include reformulating an underdetermined matrix inversion by regularization.

The inverting can include a least squares minimization.

Generating the electroanatomical representation of the patient's heart can include generating the electroanatomical representation based on the selected subset of measured signals and positions of the electrodes with respect to the endocardium surface.

In some aspects, a system for providing information about an electroanatomical representation of a patient's heart includes one or more electrodes for measuring signals at multiple positions in the patient's heart cavity over a time period including multiple heart beat cycles, at least some of the signals being in response to electrical activity in the patient's heart. The system also includes an electronic processor coupled to the one or more electrodes. The electronic processor is configured to process the measured signals to determine a metric for each of the multiple heart beat cycles, select a subset of the measured signals based on the metric associated with the heart beat cycle, and generate the electroanatomical representation of the patient's heart based on the selected subset of measured signals and positions of the electrodes.

Embodiments can include one or more of the following.

The metric comprises a beat metric.

At least one of the one or more electrodes can be configured to measure a signal indicative of tissue proximity.

The signal indicative of tissue proximity can be a force measurement.

The signal indicative of tissue proximity can be an impedance measurement.

The electronic processor can be further configured to process the signals to determine a the metric by processing the signals to determine a measure of tissue proximity and select the subset of the signals based on the metric by selecting the subset of signals based on the measure of tissue proximity.

The electronic processor can be further configured to select the subset of signals indicative of the measure of tissue proximity by selecting signals within about 3 mm of the endocardium surface.

At least one of the one or more electrodes can be configured to measure a force on a catheter.

At least one of the one or more electrodes can be configured to measure a signal indicative of contact with the endocardium surface and the electronic processor can be further configured to process the signals to determine the metric by processing the signal indicative of contact with the endocardium surface to determine a force measure and select the subset of the signals based on the metric by selecting the subset of signals having a force measure within a predetermined range.

The electronic processor can be further configured to select the subset of signals having a force measure within a predetermined range by selecting signals having a force measure above a first threshold and below a second threshold.

The metric can be an indication of contact with the endocardium surface.

The metric can be an indication of signal propagation and the electronic processor can be further configured to select the subset of the measured signals based on the metric by selecting the subset of signals having metrics associated with a desired signal propagation.

The one or more electrodes can include a first electrode located in a first stable location configured to measure a first signal and a second electrode located in a second stable location that is spaced apart from the first stable location configured to measure a second signal and the electronic processor can be further configured to process the measured signals by determining a timing difference between activations in the first signal and the second signal and select the subset of the measured signals by selecting the subset of signals having a timing difference within a predetermined range.

The electronic processor can be further configured to select the subset of the measured signals based on the metric by selecting a subset of the measured signals for beats during which capture of a pacing signal occurred.

The one or more electrodes can include electrodes configured to measure a pacing signal and a second signal located in a stable location and the electronic processor can be further configured to process measured signals by determining a timing difference between the pacing signal and an activation in the second signal, the timing difference providing information associated with capture of the pacing signal by the patient's heart.

The metric can be an indication of ventrical activation and the electronic processor can be further configured to select the subset of the measured signals based on the metric by selecting the subset of signals having metrics associated with the absence of ventricular activation.

The beat metric can be an indication of a far field signal and the electronic processor can be further configured to select the subset of the measured signals based on the metric by selecting the subset of signals having metrics associated with the absence of the far field signal.

The metric can be an indication of electrogram consistency for spatially correlated signals, with the spatially correlated signals being measured at similar locations within the heart cavity and the electronic processor can be further configured to select the subset of the measured signals based on the metric by selecting the subset of signals having an electrogram consistency that is within a predetermined range.

The electronic processor can be further configured to select process the signals to determine the metric by processing location information associated with the signals to determine signals measured at similar locations and processing the signals measured at similar locations to determine a measure of similarity between the signals measured at the similar locations and select the subset of the measured signals comprises selecting the subset of signals based on the measure of similarity.

The metric can be an indication of electrogram consistency for temporally related signals and the electronic processor is further configured to select the subset of the measured signals based on the metric by selecting the subset of signals having an electrogram consistency that is within a predetermined range.

The electronic processor can be further configured to process the signals to determine the metric by processing the signals to determine a measure of similarity between at least two spatially correlated signals and selecting the subset of signals comprises selecting a subset of signals based on the determined measure of similarity between the at least two spatially correlated signals.

The electronic processor can be further configured to process the signals to determine the metric by processing the signals to determine a measure of similarity between at least two temporally correlated signals and selecting the subset of signals comprises selecting a subset of signals based on the determined measure of similarity between the at least two temporally correlated signals.

The metric can be an indication of rapid changes in an electrogram.

The one or more electrodes can be one or more electrodes on an intracardiac catheter.

The electronic processor is further configured to comprising synchronize the signals measured at the multiple positions with one another according to a heart beat cycle.

The electronic processor can be configured to generate an electroanatomical representation of the patient's heart by determining physiological information at multiple locations of the endocardium surface based on the measured signals at the multiple positions by processing the synchronized signals.

The electronic processor can be configured to generate the electroanatomical representation of the patient's heart by determining physiological information by processing the measured signals based at least in part on a mathematical operator approximating Laplace's equation.

The electronic processor can be further configured to display at least a portion of the electroanatomical representation of a patient's heart.

The electronic processor can be configured to generate the electroanatomical representation of the patient's heart by determining physiological information at multiple locations of the endocardium surface by applying a transformation function to the signals, wherein the transformation function relates signals measured from at least some of the different positions in the heart cavity to the physiological information at the multiple locations of the endocardium surface.

The determination of the physiological information at the multiple locations of the endocardium surface can include determining the transformation function by calculating a forward transformation for relating the physiological information at the multiple locations of the endocardium surface to the signals measured for the different positions of the catheter in the heart cavity and inverting the forward transformation.

The electronic processor can be further configured to select a subset of less than all of the signals and generating an electroanatomical representation of the patient's heart based on the selected subset of less than all of the signals.

It is believed that the systems and methods described herein, can provide quick and automatic ways to aggregate data acquired over multiple cardiac cycles while keeping the data synchronized and selecting only data that can be used to generate a reliable electroanatomical map.

It is also believed that the systems and methods described herein, can provide quick and automatic ways to generate annotation information and display the annotation information with the electroanatomical map.

Embodiments of the system may also include devices, software, components, and/or systems to perform any features described above in connection with the methods described herein.

Embodiments of the methods and systems generally disclosed herein can be applied to determining the position of any object within an organ in a patient's body such as the patient's heart, lungs, brain, or liver.

As used herein, the "position" of an object means information about one or more of the 6 degrees of freedom that completely define the location and orientation of a three-dimensional object in a three-dimensional coordinate system. For example, the position of the object can include: three independent values indicative of the coordinates of a point of the object in a Cartesian coordinate system and three independent values indicative of the angles for the orientation of the object about each of the Cartesian axes or any subset of such values.

As used herein, "heart cavity" means the heart and surrounding tissue.

Unless otherwise defined, all technical and scientific terms used herein have the same meaning as commonly understood by one of ordinary skill in the art to which this invention belongs. In case of conflict with documents incorporated herein by reference, the present document controls.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Like reference symbols in the various drawings indicate like elements.

DETAILED DESCRIPTION

Figure 1:
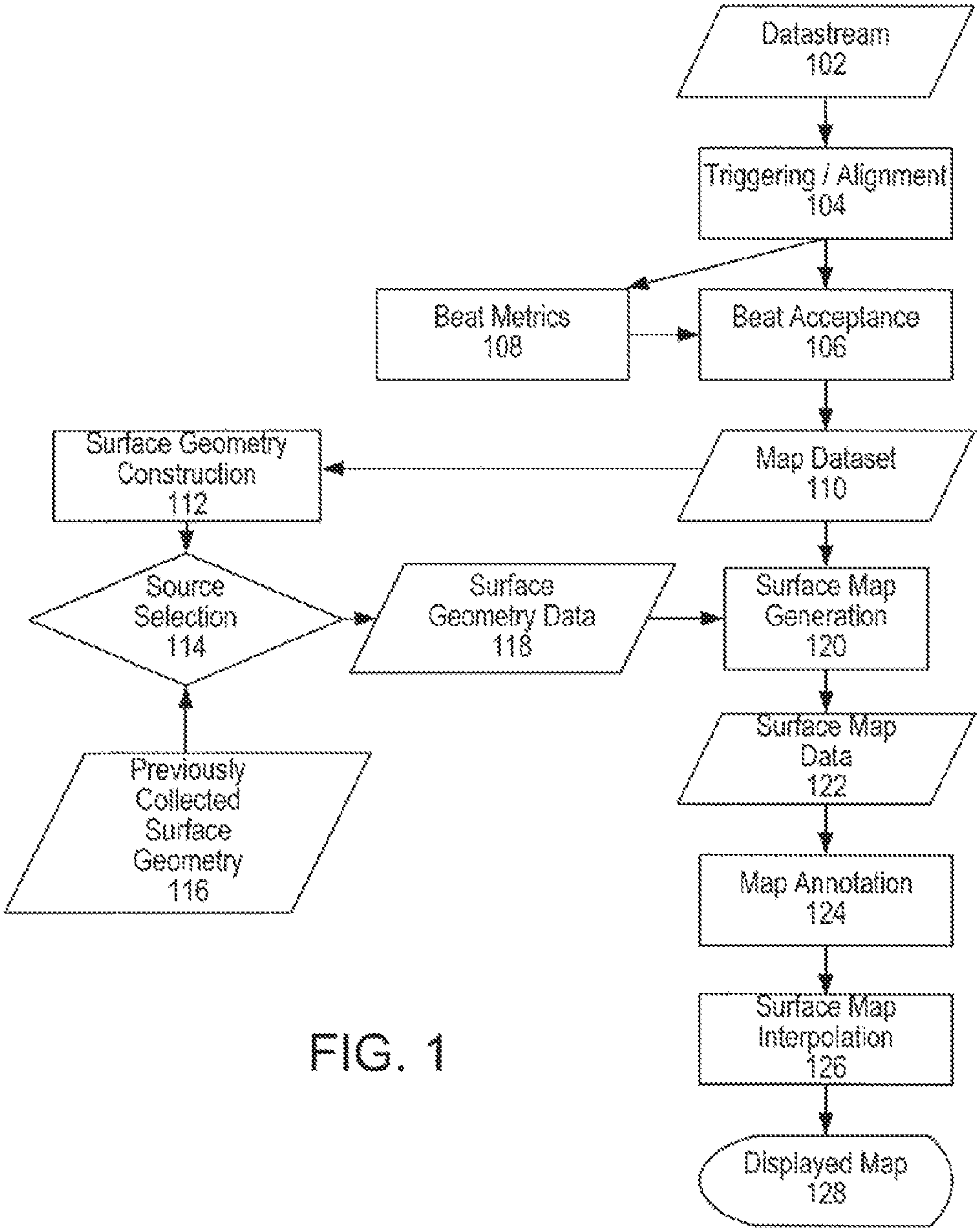
FIG. 1 is a flow chart of an exemplary electro-anatomical mapping process.

Systems and methods are disclosed herein that provide a way to automatically integrate measurements taken over multiple heart beats into a single cardiac map while selecting and keeping only heart beats that can be used to generate a reliable electroanatomical map. Systems and methods are also disclosed herein that provide a way to automatically generate annotation information and display the annotation information with the electroanatomical map.

Systems and methods for automating the process of generating an electroanatomical map are disclosed herein. Electroanatomical maps can be used to guide the catheter ablation treatment of cardiac arrhythmia by providing information on the anatomy and cardiac excitation to help pinpoint the source of the arrhythmia. Existing mapping methodologies rely on numerous manual operator inputs limiting mapping speed, repeatability and resolution.

Thousands of electrogram measurements are necessary in order to map a given cardiac chamber with sufficient accuracy and resolution. Automation during data acquisition and map construction enables a computer to process the large amount of data in a timely and accurate manner. Systems and methods for automating the generation of reliable electroanatomical maps using a computer are described herein.

In general, cardiac mapping systems can be used for automatically generating different types of maps (e.g., with limited human intervention). Such maps display electrical data, anatomical data, or a combination of both, and aid physicians in determining the source of arrhythmias and in guiding therapeutic treatment, often in the form of RF ablation. An exemplary mapping system is described, for example, in U.S. Pat. No. 7,515,954, entitled "NON-CONTACT CARDIAC MAPPING, INCLUDING MOVING CATHETER AND MULTI-BEAT INTEGRATION" and filed Jun. 13, 2006, the contents of which is incorporated by reference herein in its entirety.

Some non-automated (e.g., manual) mapping methodologies can involve operator review and input for each set of incoming data. In order to allow adequate time for review of the incoming data, a limited set of information is provided to the operator for interpretation in order to decide which data to add to the mapping dataset. While manual mapping allows the generation of maps, the mapping process is relatively time consuming and the quality of the maps highly operator dependent. Cardiac cycle length typically ranges from 0.15-1.5 s, a rate too fast for an operator to manually review all incoming data during mapping. As a result, with manual mapping most collected data is ignored thereby slowing the mapping process and limiting map accuracy. In addition, manual mapping relies on quick analysis performed by the operator which can lead to inconsistencies due to varying level of operator skill and operator error. Systems and methods for automating the process of generating and possible annotating an electroanatomical map are disclosed herein.

The impact of the application of the system and method described herein on mapping time and map resolution can be high. For example, based on reported literature values, in manual point by point mapping systems, the rate of point acquisition is 3 points per minute. Following a typical mapping effort lasting 30 minutes, a map containing roughly 90 data points on the cardiac surface is obtained. Using a multi-electrode mapping catheter such as described in U.S. patent application Ser. No. 12/005,975 entitled "CARDIAC MAPPING CATHETER" and filed on Dec. 18, 2007, the contents of which is incorporated by reference herein in its entirety, in 14 human patients has led to an average of 500 points per minute, with typical mapping times of 10 minutes providing 5,000 data points on the cardiac surface.

FIG. 1 shows a flow chart of an exemplary automated electro-anatomical mapping process. A data stream (102) containing multiple signals is first input into the system. The datastream may include signals such as intracardiac electrograms, surface electrocardiograms (ECG), electrode location information originating from a variety of methodologies (magnetic, impedance, ultrasound, real time MRI, etc.), tissue proximity information, catheter force information (force spring sensing, piezo-electric sensing, optical sensing etc.), catheter electrical coupling information, respiration phase and other physiological information, etc. For the generation of specific types of maps, one or more signals may then be used as reference to trigger and align the data stream relative to the cardiac, other biological cycle or an asynchronous system clock resulting in beat datasets (104).

For each incoming beat dataset a number of beat metrics are computed (108). Beat metrics may be computed using information from a single signal, spanning multiple signals within the same beat or from signals spanning multiple beats. The beat metrics provide multiple types of information on the quality of the specific beat dataset or likelihood that the beat data is good for inclusion in the map dataset. Once beat metrics are computed, a beat acceptance process (106) aggregates the criteria and decides which beat datasets will make up the map dataset (108).

A surface map generation process (120) is then employed to generate surface map data from the map dataset and surface geometry data. Surface geometry data may be generated concurrently during the same data acquisition process using identical or different triggering and beat acceptance metrics employing a surface geometry construction process (112). This process constructs surface geometry using data such as electrode locations and catheter shape contained in the data stream. Alternatively, previously collected surface geometry may be used as an input to surface map data (116). Such geometry may have been collected previously in the same procedure using a different map dataset, or using a different modality such as CT, MRI, ultrasound, rotational angiography, etc. and registered to the catheter locating system. The system selects the source of the surface geometry data (114) and provides surface geometry data (118) to the surface map generation process (120). The generation process (120) generates surface map data (122). The surface map data (122) may provide information on cardiac electrical excitation, cardiac motion, tissue proximity information, tissue impedance information, force information, or any other collected information desirable to the clinician. Once obtained, the surface map data may be further processed to annotate desired features from the underlying data, a process defined as surface map annotation (124). Desired annotations can include instantaneous potential, activation time, voltage amplitude, dominant frequency and other properties of the signal. Once computed, the annotations are displayed superimposed on chamber geometry. If the number of annotations is lower than the number of elements that make up the display of surface geometry, surface map interpolation may be employed (126). Displayed maps can be computed and displayed separately, or overlaid on top of each other (128).

Datastream

Referring back to FIG. 1, during the automated electroanatomical mapping process a data stream (102) provides a collection of physiological and non-physiological signals that serve as inputs to the mapping process. The signals may be collected directly by the mapping system, or obtained from another system using an analog or digital interface.

The data stream may include signals such as unipolar or bipolar intracardiac electrograms (EGM), surface electrocardiograms (ECG), electrode and/or catheter location information originating from a variety of methodologies (magnetic, impedance, ultrasound, fluoroscopy, real time MRI, etc.), tissue proximity information, catheter force/or contact information obtained from a variety of methodologies, catheter tip or tissue temperature, acoustic information, catheter electrical coupling information, respiration phase, blood pressure and other physiological information. In addition, the dataset may contain additional information such as catheter shape, electrode properties, etc.

Triggering

Referring back to FIG. 1, during the automated electroanatomical mapping process a triggering process (104) defines a time instance around which a window of data from the data stream is sampled. In some cases, a trigger event is detected from a physiological signal designated as a reference signal. In other cases the trigger is asynchronous to the patient and derived from a system clock. For example, when constructing an activation map it is common to use an ECG or EGM signal as a reference. When constructing an anatomical shell, however, such reference may not be necessary and system clock can provide a trigger.

When aggregating data from multiple cardiac beats to create an electroanatomical map, it is be useful to trigger off of a stable reference in the data stream. The reference provides alignment across beats to a desired phase in the cardiac cycle. In some examples, a single signal source is selected for triggering (e.g. ECG lead II) and waveform attributes such as minimum/maximum, absolute maximum, maximum/minimum slope, or first deviation from baseline are used to detect a trigger. Signal morphology attributes, catheter motion and noise sources can make it challenging to reliably and consistently trigger with such simplified schemes. Inaccurate triggering, in turn, may lead to corruption in the map dataset and resultant electroanatomical map. It is believed that using multiple signals to determine triggering can provide various advantages in comparison to triggering schemes based on a single signal.

Blanking

In some embodiments, it may be impractical to consistently trigger on a given signal using the signal's waveform alone using simple criteria. For example, when mapping in the right or left atrium it is often desirable to use a bipolar intracardiac signal as reference. To avoid timing inaccuracy, it is important for this signal to trigger on atrial rather than ventricular activation. A bipolar electrode pair positioned in the Coronary Sinus ("CS") is frequently used as a reference for this purpose. Nonetheless, depending on patient specific anatomy, the bipolar electrode pair may measure atrial and ventricular activation with comparable amplitude. As a result, when using a single signal source, it is difficult to consistently trigger on the desired atrial activation. Existing solutions to this problem include searching for a different set of electrodes and when those are not available, repositioning the catheter with the hope of finding a better trigger site. It is frequently the case that neither approach is successful. This invention provides a means to overcome this problem using an additional signal with dominant ventricular activation as a blanking reference.

Figure 2:
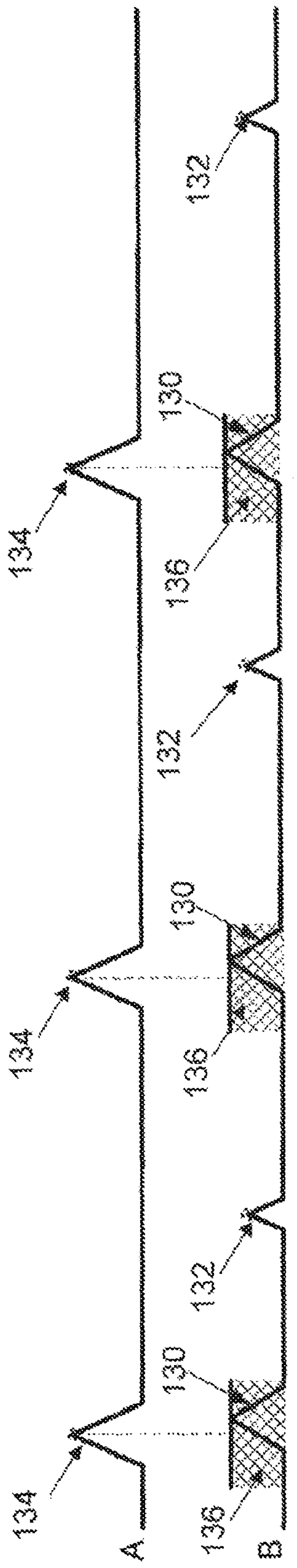
FIG. 2 shows exemplary waveforms with applied blanking windows.

FIG. 2 provides an example of this approach. Waveform B is a schematic of the waveform used for reference triggering. The waveform has two dominant activations 130 and 132, the lower amplitude activation 132 being the desirable reference trigger. Clinically, these two activations 130 and 132 can be ventricular and atrial activations measured on a bipolar Coronary Sinus electrode pair, the atrial activation 132 being the desirable trigger. In order to reliably trigger on the lower amplitude atrial signal 132, an additional waveform is employed, waveform A. In this waveform, the undesirable activation is dominant and easy to detect (e.g., as shown in activations 134). Clinically, this may be lead II of a surface ECG signal where the trigger is the R wave. This waveform can be defined as the blanking reference waveform. The timing detection algorithm can employ any of maximum, minimum, maximum or minimum derivative, deviation from baseline, etc. as a detection criteria to find the blanking reference timing of interest. Once the blanking reference is detected (e.g., once the timing of activation 134 is detected), a blanking window 136 is defined for waveform B. The blanking window 136 has a defined offset and duration relative to the blanking reference. The offset and duration are determined to be large enough so they include the entire undesirable activation duration, but not too large so as to include the desirable activation timing. Typical values when using ECG II as blanking reference waveform and Coronary Sinus as reference trigger are 40 ms for offset and 120 ms for duration. When determining the trigger in waveform B, signal is ignored during the blanking window. In this manner, the impact of the undesirable signal is effectively ignored.

It is important to note that this approach can be used with other scenarios and signals. For example, cardiac stimulation is often employed during mapping. It may be desirable to trigger off of a biological signal rather than the stimulation signal. In a manner identical to the one described above, a waveform with large stimulation signal may be employed as a blanking reference waveform. A waveform with both stimulation artifact and signal indicative of biological activation may then be used as the reference trigger.

Furthermore, there may be situations where more than one blanking reference is used to determine triggering (e.g., two blanking signals, three blanking signals, four blanking signals). For example, it is possible that both stimulator artifact and ventricular activation are present on a signal where the desired trigger is atrial. In this case two blanking references can be defined simultaneously.

In addition, rather than a blanking window, the blanking reference can define an inclusion window. In this case the reference trigger in waveform B may be determined only during the inclusion window constructed around the blanking reference in waveform A. For example, this may be desirable when mapping in the ventricle. Once again, waveform A may be ECG lead II and waveform B a bipolar set of electrodes in the Coronary Sinus. In this case, an inclusion window around the blanking reference will be used to find ventricular activation during the inclusion window in the Coronary Sinus waveform.

Figure 3:
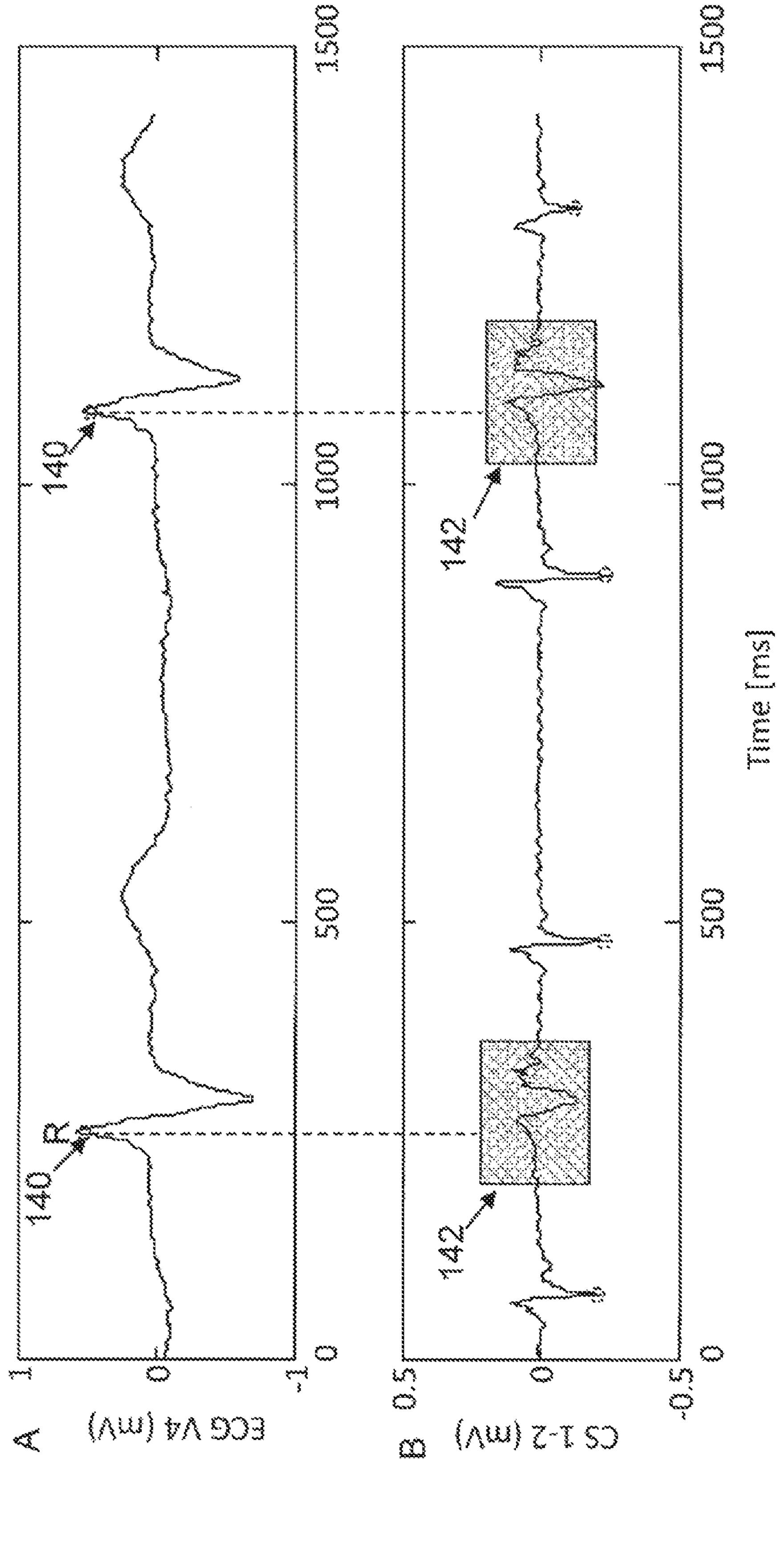
FIG. 3 shows exemplary data signals from and ECG and an electrode in the coronary sinus.

FIG. 3 shows blanking applied on signal collected from a human patient. Waveform A is the blanking reference waveform, in this case ECG lead V4. Waveform B is the CS waveform. A window 140 around the R wave 140 is applied on the CS signal. When looking for a reference trigger or activation time on this signal, the period during which the blanking window 140 exists is ignored.

Blanking is useful in triggering set-up but can also be used for annotation. For example, blanking can be applied to individual EGMs, using a common blanking waveform reference to avoid far field effects. Voltage amplitude and other annotations can also be derived from the benefit from blanking.

Powered Triggering

Figure 4:
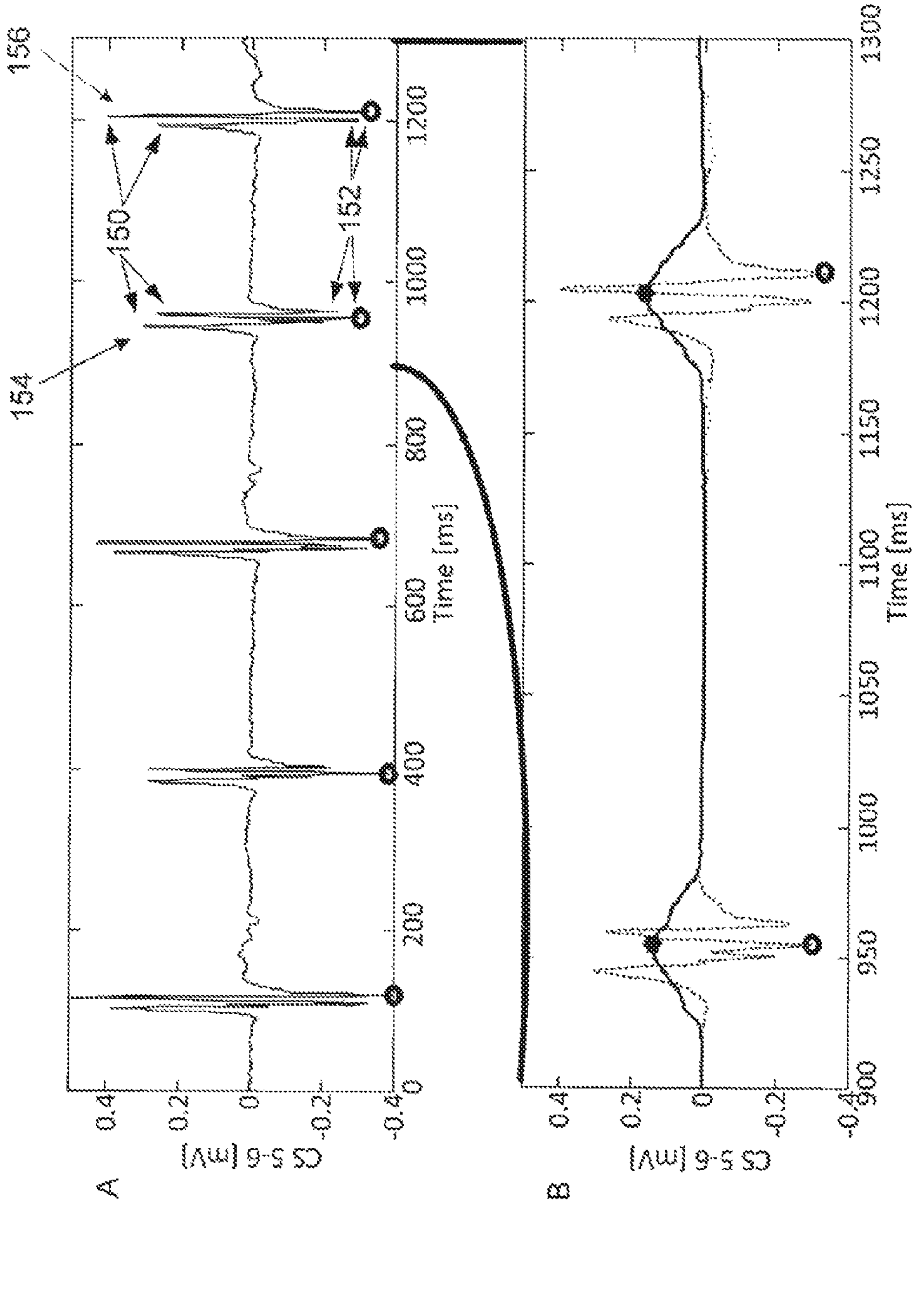
FIG. 4 shows an exemplary data signals and processed data signals.

FIG. 4 waveform A provides an example of a bipolar Coronary Sinus signal acquired in a human patient. As the waveform demonstrates, the bipolar signal may exhibit multiple upstroke components 150 and downstroke components 152 during local activation. Furthermore, the morphology of the signal may change substantially with small changes in activation and catheter movement. As shown with arrows in waveform A, the timing of the local maximum and minimum changes frequently and would lead to timing jitter in the map dataset. For example, in the activation 154 the first upstroke component would provide the local maximum while in activation 156 the second upstroke component would provide the local maximum. Similarly, in the activation 154 the first downstroke component would provide the local minimum while in activation 156 the second downstroke component would provide the local minimum. Thus, timing based on the local maximum or local minimum would experience timing jitter due to the selection of different activation times within the signal.

As before, existing solutions to this problem can include searching for a different set of electrodes and when those are not available, repositioning the catheter with the hope of finding a more stable trigger site. Systems and methods described herein can overcome this problem applying additional processing to the signal to search for a peak in instantaneous power or an equivalent measure. Such triggering will be called powered triggering.

For a given sampled signal, S(n), the equation below provides the powered triggering operator:

$$S_p(n) = \sqrt{\sum_{i=-N}^{N} [a_i \cdot S(n+i)]^2} \qquad \text{Equation 1}$$

$$a_i = \left\{ \begin{array}{c} 0 \text{ if } |i| > N \\ \frac{1}{2 \cdot N + 1} \text{ if } |i| \le N \end{array} \right\}$$

This operator squares and sums the signal over a finite window of 2·N+1 samples. Once applied, simple local maximum detection can be robustly applied as shown in FIG. 4 waveform B. Maximum derivative detection can also be applied in this case. In practice, a window duration of 70 ms was found to perform well.

This operation is an instantaneous power estimate and as such is sign invariant and less susceptible to local morphology changes. It should be appreciated that variations on this operator could be provided. Those include applying an absolute value operator or any even power to the signal. In addition, more elaborate window function such as Hanning, Kaiser, Blackman etc. or a frequency selective window could be employed.

This operator is useful in triggering set-up but can also be used for annotation. For example, the operator can be applied to individual EGMs, and the activation timing found as the maximum. Voltage amplitude and other annotations can also be derived from the powered signal.

Beat Metrics and Acceptance

Referring back to FIG. 1, following triggering on a desired signal (104) beat metrics (108) are used to determine beat acceptance (106). Each trigger event is referred to as a beat, even though the event may be triggered from non-cardiac information. In the beat metric and acceptance process, a beat window is defined around the occurrence of a trigger event. While triggering identifies a desired event in a reference signal, many additional factors affect the quality and relevance of data collected in any given beat. For example attributes such as cardiac cycle length, catheter velocity, respiration phase, patient movement, injury current etc. can affect the relevance of the data for inclusion in a map dataset for certain types of electroanatomical maps.

In order to create a map dataset, some elements of a beat acceptance scheme is automatically applied by a computer to incoming beats. The scheme applies a predetermined set of beat metrics in order to add into the map dataset only beats that meet certain criteria. In the case of a catheter with multiple electrodes a beat metric can affect the inclusion or exclusion of all information collected by the catheter during the duration of the beat. Alternatively, the beat metric can apply to and dictate the inclusion or exclusion of a subset of the information collected by the catheter. In manual mapping systems this activity is performed by the operator with limited information guiding their decision. Furthermore, beats arrive at a rate ranging 0.2-1.5 seconds, a rate too fast for operator review.

Beat metrics can be directly used by an electroanatomical mapping system to automate the mapping process. Nonetheless, the information provided by the beat metrics can also be presented and used as additional operator input in a manual mapping system.

Beat metrics may be designed to provide both a binary YES/NO acceptance decision as well as a value indicative of the acceptance level. When aggregating different beat metrics into a beat acceptance decision a logical AND can be applied to all beat metrics. If desired, a more elaborate function can be applied by the computer to either the set of binary decisions or values in order to determine if a beat is to be added into the map dataset.

Beat acceptance and beat metrics may run in real time as the data stream is arriving (e.g., the computer can process the data stream as the datastream is received). In addition, the scheme can be rerun following data collection, potentially with different parameters (e.g., the computer can re-process the data after collection). For example, a patient may present with two intermittent rhythms during mapping. During the mapping process a map dataset containing only beats with one rhythm may be collected, the other rhythm being rejected. Following the mapping process, beat metrics can be recomputed and acceptance applied to accept the second rhythm and produce a second map. Alternatively, the two rhythms can be mapped simultaneously by setting up two beat acceptance and mapping pipelines, each designed to accept and reject a different desired rhythm.

The following describes different exemplary beat metrics that can be applied to incoming beats. It should be understood that other types of beat metrics can also be applied.

Mechanically Based Metrics

Respiration

Patient respiration has a number of effects on the heart mapping system. It leads to a movement of the heart within the chest which can affect the accuracy of the catheter or electrode locating system. Respiration also causes a deformation of the heart shape which can be as high as 7 mm in certain parts of the anatomy ("A Study of the Motion and Deformation of the Heart Due to Respiration," Kate McLeish, IEEE Transactions On Medical Imaging, VOL. 21, NO. 9, September 2002). In addition, respiration can displace diagnostic catheters modifying their EGM measurement and may even slightly modulate cardiac rhythm.

As a result it is desirable to form a respiration beat metric used to detect respiration phase and collect data during a consistent period in the respiratory cycle. The beat metric can employ a number of schemes to collect respiration phase data.

In cases where a patient is mechanically ventilated, respiration phase information can be provided directly through an interface to the ventilator. Respiration can also be detected using a variety of standard means such as monitor belt and acoustic sensing.

Figure 5:
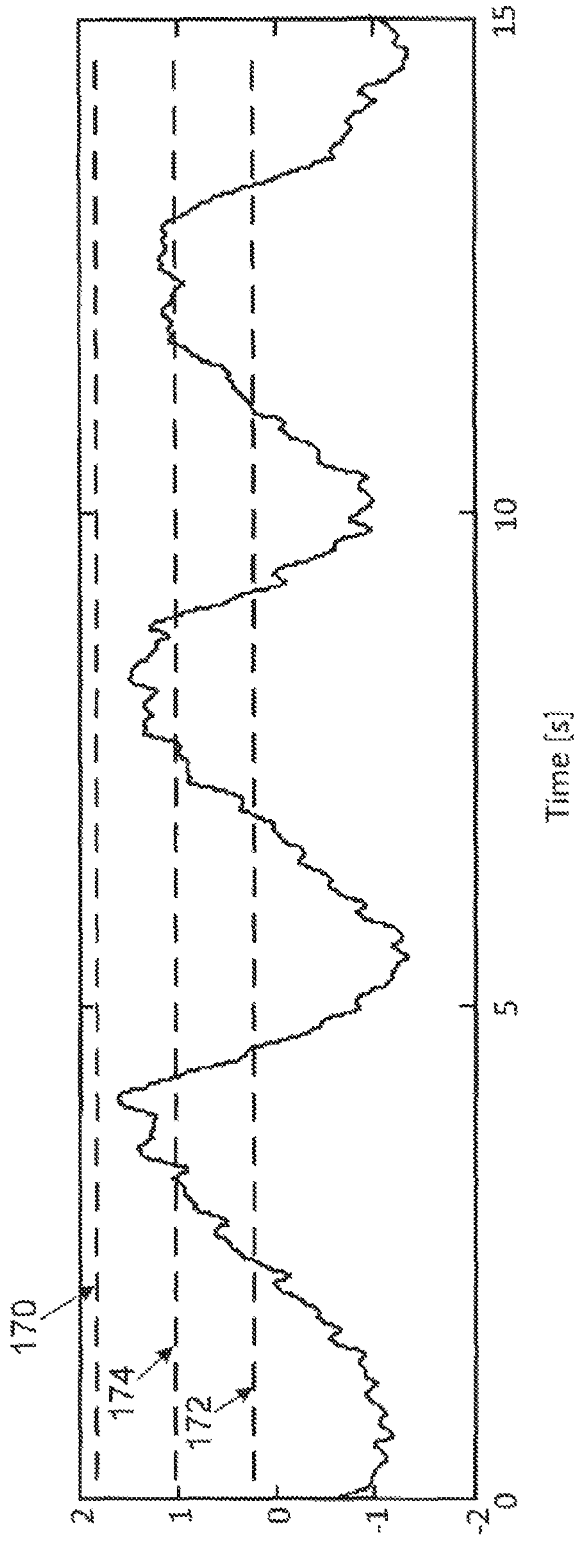
FIG. 5 show exemplary data signals measured on an electrode in the Coronary Sinus.

Particularly applicable respiration phase sensing schemes during a catheter ablation procedure include impedance detection and location sensor. In impedance detection, current injecting electrodes can be placed on the body surface or in the body and set to inject current in a desired frequency. The same current injecting electrodes, or any other electrodes, can be used to monitor to the resultant potential which will have a significant respiratory effect in it. FIG. 5 depicts the waveform measured on a body surface electrode positioned on the chest when injecting current between electrodes in the Coronary Sinus and a body surface electrode. As the figure shows, the signal is periodic. A range of values on the waveform can define the desired range and be used for thresholding as shown by the bold dotted lines 170, 172 in the figure. The beat metric value is the difference between the average value of the waveform during the beat window and the center of the desired range (e.g., as indicated by the location where the signal crosses the dotted line 174). Alternatively, the beat metric value can be the difference between the median during the window or the instantaneous value during the timing of the reference trigger and the center of the desired range. When the beat metric value is within the desired range the beat metric receives a YES decision.

Figure 6:
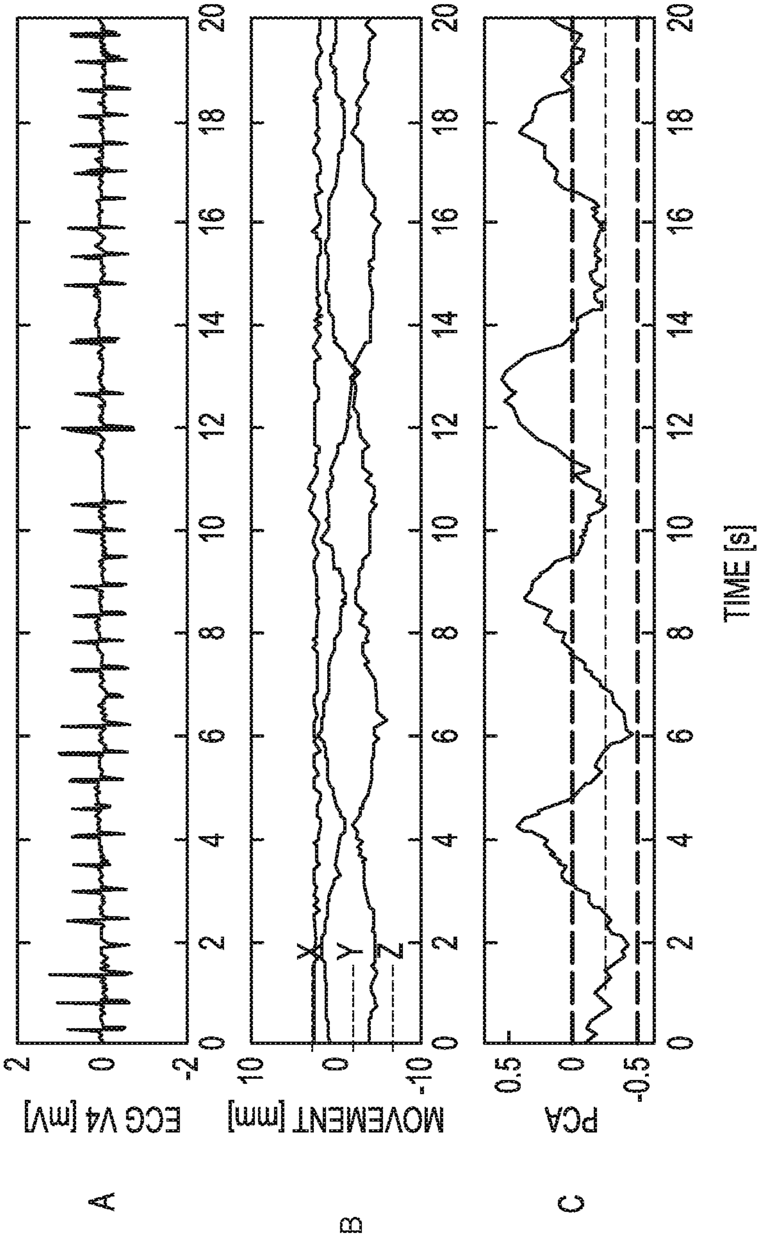
FIG. 6 shows an exemplary data signals for respiration detection.

Alternatively, a location sensor can also be placed on the chest or in the body. The location sensor may, for example, use magnetic locating technology. Sensor location can be plotted over time with a similar range thresholding scheme described above. FIG. 6 shows respiration detection using location information in a human patient. Waveform A shows ECG, and waveform B shows the corresponding X, Y and Z coordinates of a location sensor placed on the chest. In order to reduce the 3 coordinates to one waveform used for thresholding, principal component analysis is applied to the X, Y and Z coordinates. The first component is plotted in waveform C and used for thresholding. Multiple location sensors on or in the patient can also be used in a similar manner.

Tissue Proximity

An important problem in the construction of electroanatomical maps is tissue proximity determination. When a mapping catheter is maneuvered in the heart, it is difficult to determine if it is in contact or in proximity to cardiac tissue. Various methods including EGM review, ultrasound, fluoroscopy and tactile feel can be employed to determine contact. However, those may lack proper sensitivity and specificity and may be difficult to incorporate in an automated mapping procedure. For example, when the catheter is in contact with infracted tissue, EGM properties and mechanical catheter movement may be indistinguishable from those when the catheter is not in contact. Knowledge of tissue proximity is valuable for both the constriction of the anatomical and electrical map.

A variety of methods can be employed to determine tissue proximity. For example, tissue proximity assessment using impedance information such as described in U.S. patent application Ser. No. 12/437,794 or coupling for example as described in U.S. patent application Ser. No. 12/096,071, the contents of each of which are hereby incorporated by reference in their entirety can also be used as inputs for this beat metric. In the case of impedance information, a current injecting electrode on the mapping catheter injects a current. Measurements collected by the injecting electrode and/or other potential measuring electrodes can be used to determine information about cardiac tissue and its proximity to the catheter and its electrodes. This information can subsequently be provided on a per electrode basis, or globally for the entire catheter.

A surface geometry construction algorithm may require electrode positions with close wall proximity as an input. Tissue proximity information can be used in this case with threshold values such that the computer system makes a determination about whether to accept a beat based on the tissue proximity information and only accept beats and/or electrode locations whose tissue proximity values indicate small distance to the wall. For example, a threshold of 3 mm may be used.

Similarly, for electrical mapping, only beats and/or electrode locations where tissue proximity information indicates proper wall distance are desired in the map dataset. Range thresholding can be similarly applied by the computer system to generate a beat metric and decision to include only those measurements in the map.

Contact force between the catheter and the wall can also be determined and used as metric. Force can be measured using a number of technologies including piezoelectric crystals for example as described in U.S. patent application Ser. No. 11/553,965, location information on sensors separated by a resilient deformable member at the catheter tip for example as described in U.S. patent application Ser. No. 11/868,733, and optical sensing for example as described in U.S. patent application Ser. No. 11/237,053.

Force values can be divided into 3 ranges. The first range is low force, e.g. F<8 g, which indicates no wall contact. The second range is an intermediate amount of force, e.g. 8 g<F<40 g, which indicates proper wall contact. The third range is high force, e.g. F>40 g, which indicates excessive force possibly tenting and deforming cardiac anatomy.

Surface geometry construction algorithms used to create chamber anatomy may require a map dataset with catheter positions both inside the chamber and with proper wall contact. In this case, force information can be directly used as a beat metric with a range thresholding scheme designed to only accept beats whose force is under the excessive force threshold. For surface geometry construction algorithms that require positions with proper wall contact alone as an input, force information can be used with threshold values that only accept beats whose force value indicates proper wall contact.

For electrical mapping, only beats where the catheter force information indicates proper wall contact are desired in the map dataset. Range thresholding can be similarly applied by the computer system to generate a beat metric and decision to include only those measurements in the map.

Catheter Movement

The mapping catheter is moved by the clinician to different sites in order to collect measurements in multiple locations. In addition, the catheter experiences motion due to cardiac contraction. The mapping system may assign a single location to electrodes during the beat window using averaging, median or gating to the reference trigger or window center. Excessive catheter motion during the beat window may lead to inaccuracy in the location used to generate the map.

A beat metric can be defined to use the catheter velocity as an input. Using a range thresholding scheme described above excessive catheter motion can automatically rejected from the map dataset (e.g., automatically rejected by the computer system without substantial human interaction).

Patient Movement

Similarly to respiration, patient movement can affect cardiac anatomy and catheter tracking accuracy. A beat metric can be used to detect patient motion and reject data during and/or following patient movement.

In the case of an external field generator, a single or multiple location sensors can be place on the body surface or in the body in a stable location providing patient location reference. The baseline position of the patient location reference can then be recorded. Once mapping begins, the distance between the baseline position and current position of the patient location reference can be generated using a range thresholding scheme. The patient location reference and thresholding can be completed automatically by a computer system based on an algorithm that does not require substantial human input.

Electrogram/Electrocardiogram Based Metrics

Various factors can affect the consistency of the electrical propagation sequence in the heart during mapping. A few examples include, intermittent rhythm, pacing failing to capture, and catheter physical contact leading to premature contractions. It is therefore critical to verify that the underlying rhythm is the one desired for mapping before adding beats to the map. Different metrics can be used to accomplish this using a computer system. The computer system can receive data inputs, analyze the data, and make a determination about whether to include collected data in an electroanatomical map and/or whether to provide an annotation based on the observed consistency of the electrical propagation sequence in the heart.

Cycle Length

The period of time between reference triggers is defined as cycle length. Cardiac cycle length typically ranges 0.2-1.5 s. During an unstable rhythm, cycle length is likely to vary across beats. Conversely, during a stable rhythm, cycle length is expected to stay stable within a certain tolerance.

Cycle length can be computed by the computer for every incoming beat. Because a computer system (as opposed to a human operator) analyzes the incoming signals to compute cycle length, the determinations can be made in real time without delaying collection of the data. One of two schemes, absolute and relative, can be used as in a range thresholding scheme to derive a beat metric from it. In an absolute scheme, a cycle length value is defined and the computer compares all incoming beats to that cycle length value. The value can be measured while the desired rhythm is taking place. In other examples, the computer system can execute a relative scheme by comparing the current cycle length to the one of the preceding beat, or some other weighted function of neighboring beats. Based on the cycle length information, the computer system can determine whether to include the data from a particular cycle in the electroanatomical map.

Propagation Reference

While cycle length is a powerful metric for detecting rhythm, it is a global measure that samples a single electrogram. As such, cycle length does not verify the propagation sequence in the heart chamber and may allow beats with different underlying rhythms to be included in the electroanatomical map. The computer system can use a propagation reference to provide additional validation that the desired propagation sequence is taking place by measuring the relative timing between a second cardiac signal and the reference trigger. The propagation reference uses the same triggering scheme as the reference trigger, and can use the same criteria (e.g., minimum/maximum) and enhancements (e.g., blanking) when triggering. For example, in one case the reference trigger can be a bipolar signal from the CS while propagation reference comes from bipolar electrodes in the right atrial appendage. Once the timing of both signals is detected, their relative timing can be used as a beat metric. In another example pacing may be used. In this case the reference trigger may be the stimulator signal while the propagation reference can be a biological signal. Similar to the previous example, if pacing is taking place in the CS, a bipolar signal from the right atrial appendage can be used as the propagation reference. This case can provide particular advantages because the propagation reference may be used to verify pacing capture. When pacing, cycle length alone may be totally dependent on the stimulator input and as such provide no useful physiological information for mapping.

Figure 7:
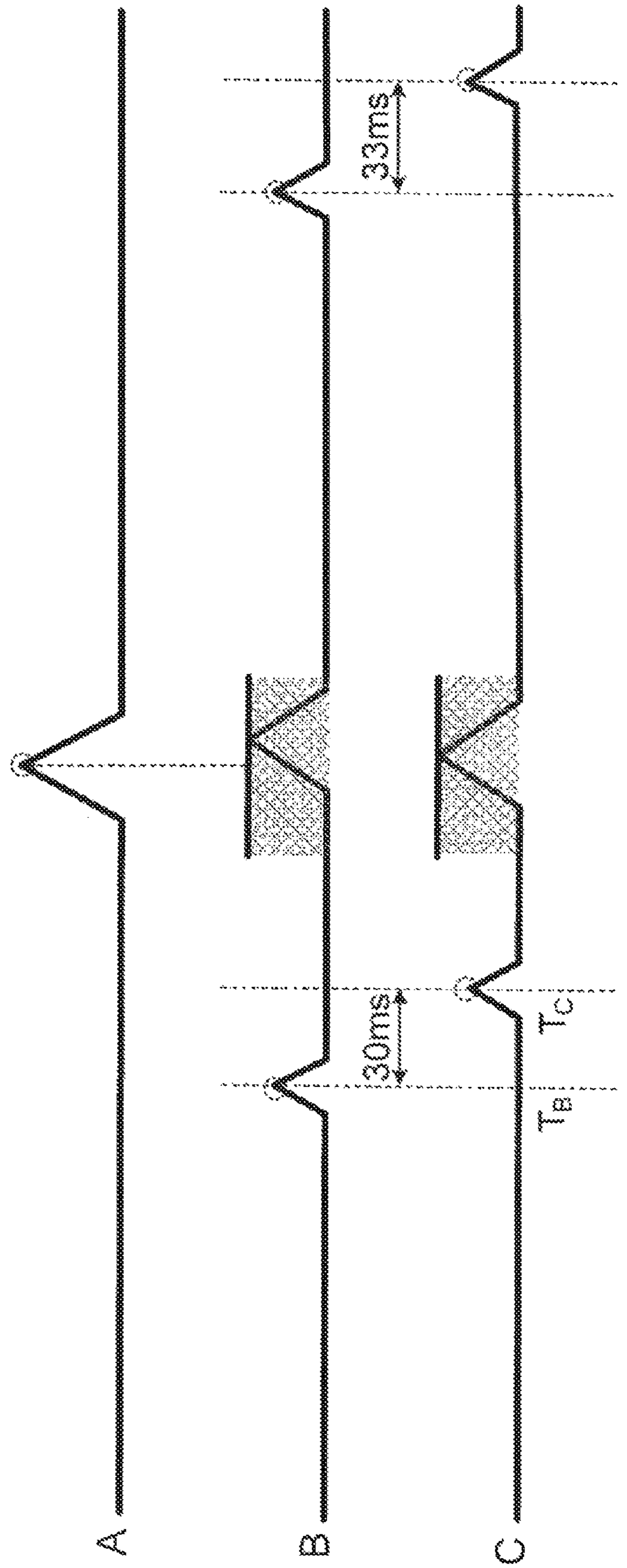
FIG. 7 shows an exemplary data signals for propagation time detection.

FIG. 7 provides a schematic example of the above. Waveform A is the blanking waveform used to provide a blanking trigger as previously described. Waveform B is the reference trigger and waveform C is the propagation reference. The relative timing between the triggers in waveforms B and C is used as a baseline and deviation from the baseline is used as beat metric. In this case the chosen relative timing is 30 ms. When the computer system determines the difference in timing between the reference trigger and the propagation reference exceeds a threshold the computer system rejects the beat and the beat signals from the beat are not included in the data set used to generate the electroanatomical map. For example, looking at the figure, if $|T_c-T_B-30 \text{ ms}|\leq 5$ ms the beat is accepted.

Similar to cycle length, either an absolute baseline difference or a relative difference can be used by the computer system for a metric. In the case of an absolute difference, an initial timing difference is used as baseline while the desired rhythm is observed. The computer system compares the timing difference of subsequent beats to the baseline value. A range thresholding scheme is then applied to derive a value and decision for the beat metric. The computer system can also calculate a relative difference and use the relative difference in this case such that the relative timing of the current beat is compared to that of the previous one.

It should be understood that more than two EGMs can be compared to verify propagation sequence. A number of propagation references can be defined each of which provides a baseline value. The beat metric can be an average of the differences.

Furthermore, waveform aspects other than timing alone can be used to verify a consistent relationship between EGMs. For example, a mathematical operator such as the one described in Equation 1 can be applied by the computer system on the propagation reference waveform. As described, the operator reduces the deflections in the waveform and provides a measure of local activation timing and energy. Subsequently, correlation or root-mean-squared difference can be applied as the metric.

Far Field Overlap

Electrogram recordings aim to measure an electrical signal emanating from tissue close to the electrode. Nonetheless, electrodes can pick up signal from tissue that is further away, particularly if the activation in local tissue is substantially smaller in amplitude than that of the signal that is further away. The signal picked up by the electrode from tissue that is further away is called far field signal. When annotating electrogram recording in an electroanatomical mapping system, it is important to annotate properties of local tissue, rather than those of the far field component. For example, when collecting recordings in certain areas in the atria (particularly when close to the tricuspid and mitral annulus) ventricular far field signal may dominate the recordings, even when nearby atrial tissue is healthy.

In certain rhythms, particularly fast rhythms, a far field component may be present on a recording during some beats but not during others. Examples include, atrial and ventricular dissociation, or an n:1 (n>1) relationship between the two. In those cases it is possible to define a beat metric that rejects those beats that overlap with the presence of a far field signal and avoid having the EGMs mis-annotated. The computer system can analyze incoming signals to determine the presence of a far field component. For example, an additional data signal can be measured to detect the presence of the far field signal. If the far field signal is detected, the computer system can use the timing of the detected signal to provide a blanking window during which data from the EGM data is discarded. Thus, if a significant far field component is detected; the computer system discards the data (e.g., not include the data from the beat in the data set used to generate the electroanatomical map).

Figure 8:
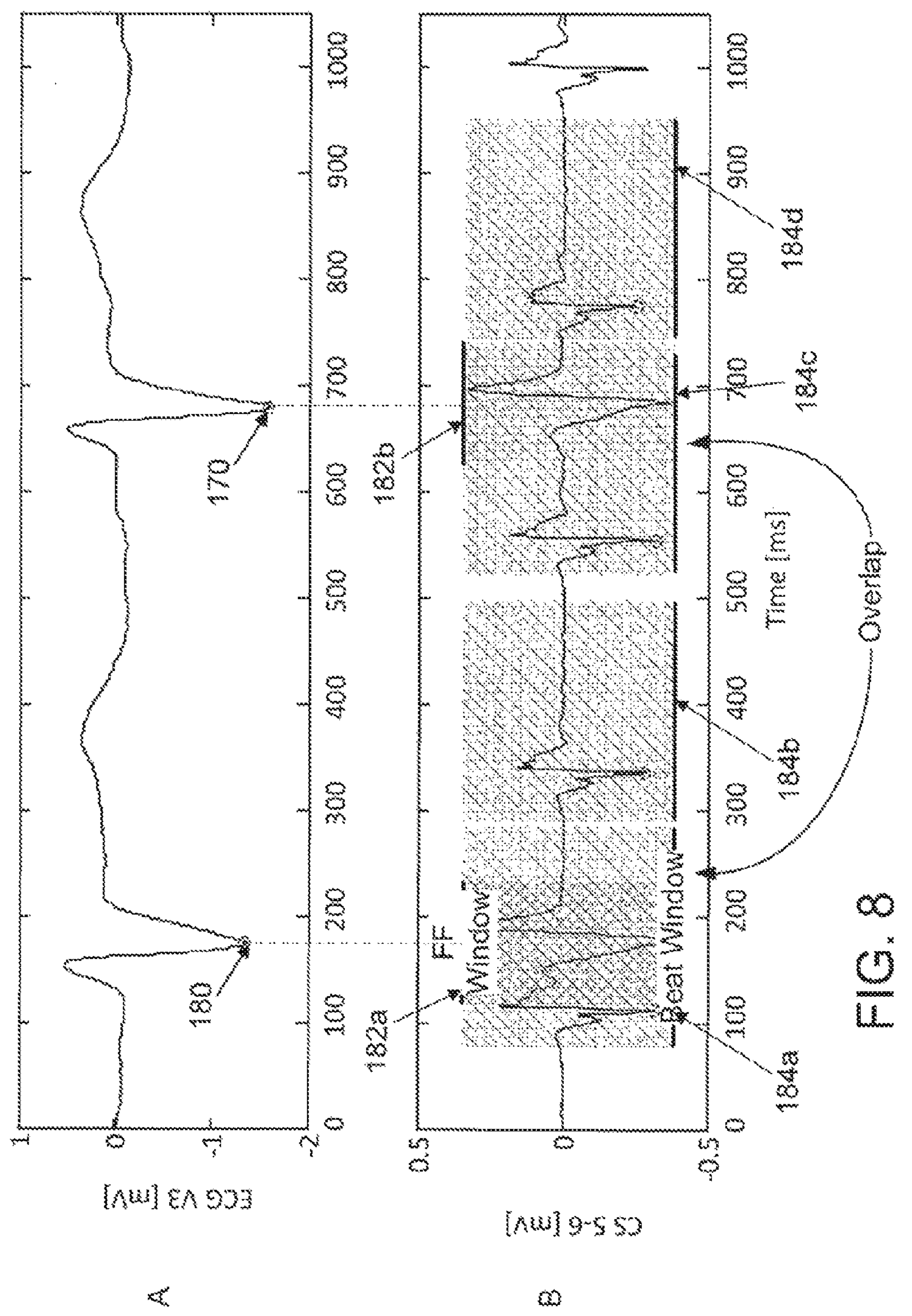
FIG. 8 shows an exemplary data signals for far field overlap detection.

FIG. 8 shows ECG and EGM recordings from an atrial tachycardia patient with 2:1 atrial ventricular conduction (as shown in signals A and B, respectively). Ventricular activation is detected from the ECG signal in waveform A. The detected signal 180 from the ECG is used by the computer system both as a blanking reference and as a far field rejection reference. The blanking reference is used to robustly trigger on atrial activation in the CS signal in waveform B which is used as a reference trigger, as discussed previously. A beat window is defined around the reference trigger (e.g., beat windows 184*a*, 184*b*, 184*c*, and 184*d*). In this example, the beat window spans is slightly less than the full tachycardia cycle length (90%). In addition, a far field rejection window 182*a*, 182*b* is defined by the computer system around the far field rejection reference 180, in this case spanning 110 ms. The beat metric value calculated by the computer system is the overlap between the beat window (e.g., beat windows 184*a*, 184*b*, 184*c*, and 184*d*) and the far field rejection window (e.g., windows 182*a*, 182*b*). Whenever the overlap exceeds 0 ms, for example, the metric can return a NO decision and the beat whose window contains ventricular activation is automatically rejected by the computer system. In this example, far field rejection window 182*a* overlaps with beat window 184*a* and, far field rejection window 182*b* overlaps with beat window 184*s*. Due to the overlap of the far field rejection window with beats 182*a* and 182*c*, the data from beats 182*a* and 182*c* is discarded and not used by the computer system to generate the electroanatomical map.

EGM Consistency

In some cases it is important to use attributes of electrograms collected by the mapping catheter as beat metrics. For example, injury current is a local change of activation which can result from mapping catheter tissue contact. In the case of injury current, EGMs recorded by the mapping catheter will be altered, while EGMs on other catheters and the rhythm remain unchanged. EGMs containing injury current can therefore be mis-annotated by the mapping system. It is therefore believed to be valuable to provide a beat metric in which the computer system automatically monitors the EGMs measured by the mapping catheter. One such beat metric is EGM consistency.

EGM consistency looks to verify that measured EGMs are consistent within a certain period of time or location. One type of EGM consistency metric can be EGM correlation between the current and previous beat. In this metric, the computer system correlates the EGM in each electrode on the mapping catheter to that of the previous beat (e.g., signals with a temporal relationship are compared to one another). An average correlation across all electrodes is then determined by the computer system. If the average correlation exceeds a certain value (e.g., 0.7) the beat is accepted. This metric has a good probability of eliminating recording corruptions that are intermittent, such as injury current discussed above. In addition, this metric is able to reject beats when the catheter moved very quickly since the recorded EGMs are likely to change as the catheter is moved.

Rather than the previous beat, EGMs can alternatively be compared to those previously added to the map in a nearby location (e.g., signals with a spatial relationship are compared to one another can be correlated by the computer system).

It is important to note that other methods can be applied to determine EGM consistency. For example the average root-mean-square of EGMs across all or some of the electrodes in neighboring beats or locations can be computed by the computer system. In addition, attributes of the EGMs, rather than EGM themselves can be compared for consistency. An example of such measure would be the detection of activation time on each EGM and the computation of change in activation time across electrodes in neighboring beats computed.

Is it also important to note that this metric can be applied on a per electrode, rather than per beat basis.

Surface Geometry Construction

The surface geometry construction algorithm generates the anatomical surface on which the electroanatomical map is displayed. Surface geometry can be constructed using a system as described U.S. patent application Ser. No. 12/437,794 entitled "Impedance Based Anatomy Generation" and filed on May 8, 2008, the contents of which is incorporated by reference herein in its entirety.

Alternatively, an anatomical shell can be constructed by the computer system by fitting a surface on electrode locations that are determined either by the user or automatically to be on the surface of the chamber. In addition, a surface can be fit on the outermost electrode and/or catheter locations within the chamber.

As described, the map dataset from which the surface is constructed can employ identical or different beat acceptance criteria from those used for electrical and other types of maps. The map dataset for surface geometry construction can be collected concurrently with electrical data or separately.

Surface geometry can be represented as a mesh containing a collection of vertices (points) and the connectivity between them (e.g. triangles). Alternatively, surface geometry can be represented by different functions such as higher order meshes, NURBS, or curvilinear shapes.

Surface Map Generation

The combination of map dataset and surface geometry data allows for surface map generation. The surface map is a collection of values or waveforms (e.g. electrograms) on the surface of the chamber of interest, whereas the map dataset can contain data that is not on the cardiac surface. One approach for processing the map dataset and surface geometry data to obtain a surface map dataset is described in U.S. Pat. No. 7,515,954, entitled "NON-CONTACT CARDIAC MAPPING, INCLUDING MOVING CATHETER AND MULTI-BEAT INTEGRATION" and filed Jun. 13, 2006, the contents of which is incorporated by reference herein in its entirety.

Alternatively or in combination with the method above, an algorithm that applies acceptance criteria to individual electrodes can be employed. For example, electrode locations exceeding a set distance (e.g. 3 mm) from surface geometry can be rejected. Another algorithm can incorporate tissue proximity information using impedance for inclusion in the surface map data. In this case only electrode location whose proximity value is $<3$ mm would be included. Additional metrics of the underlying data can also be used for this purpose. For example, EGM properties similar to beat metrics can be assessed on a per electrode basis. In this case metrics such as far field overlap, EGM consistency, can be used.

It should be understood that variations on the method to project points from the map dataset to the surface or to select appropriate points can exist.

Map Annotation

Once data is collected into surface map data, attributes relating to the collected data may be automatically presented to the user. These attributes can be automatically determined and applied to the data by the computer system and are referred to herein as annotations. Exemplary annotations include activation time, the presence of double activation or fractionation, voltage amplitude, spectral content, etc. Due to the abundance of data available in automated mapping (e.g., mapping completed by the computer system with minimal human input related to the incoming data), it is not practical for the operator to review and annotate data manually. However, human input can be a valuable addition to the data, and so when user input is provided it is necessary for the computer system to automatically propagate and apply it to more than one data point at a time.

It is possible to use the computer system to automatically annotate activation time, voltage, and other characteristics of individual electrograms. Activation time detection uses methods similar to those previously described to detect a trigger and can similarly benefit from the use of blanking and powered triggering operator.

Spatial Consistency

To further improve accuracy, in some cases it is useful to consider neighboring electrograms during annotation. One form of considering neighboring electrograms is spatial consistency: the computer system automatically adjusts annotations to improve physiological plausibility and reduce map noise by making the annotations more spatially consistent.

For activation time mapping, three common conditions benefit from spatial consistency:

Along a line of conduction block, electrograms frequently exhibit two or more distinct deflections. Due to small variations in electrode position, orientation, and motion, natural variation in activation strength, and electrical noise, the strength of the deflections within electrograms will vary between beats even for a catheter held in the same nominal location. For electrograms with multiple deflections, this variation in deflection strength causes automatic timing annotation to randomly switch between the deflections when the strengths of those deflections are similar. This results in jagged contours and mottling of the activation map along the line of block which is physiologically improbable or impossible. This map noise may hinder understanding of the activation pattern. In order to reduce the effects of multiple deflections, the computer system automatically compares the activation timing determined for the multiple beats and modifies the timing to select a different deflection when differences between temporally correlated signals exist.

For macroreentrant circuits, the beat window should be close to the typical cycle length to show the activation pattern for the entire chamber. Due to normal cycle length variation, some cycles will be slightly shorter than the beat window. In some regions, the electrograms measured during these shorter cycles will have deflections at both the start and end of the beat window, where the deflection at the end is actually the next beat. Since the deflection strength at the start and end is similar, automatic timing annotation may switch between the start and end of the cycle. This introduces mottling of the activation map in the region where the activation is transitioning from the end to the start of the beat window.

In regions of fractionation, electrograms may have long periods of relatively weak but similar strength activation. This occurs because the electrode is measuring activation that wends along a slow and convoluted path through mostly scar tissue near the electrode. Automatic timing annotation in these regions may appear entirely random because the selected time corresponds to an arbitrary peak in the fractionated electrogram, not the nominal activation time at that location. This obscures the direction of propagation through these regions.

Figure 9:
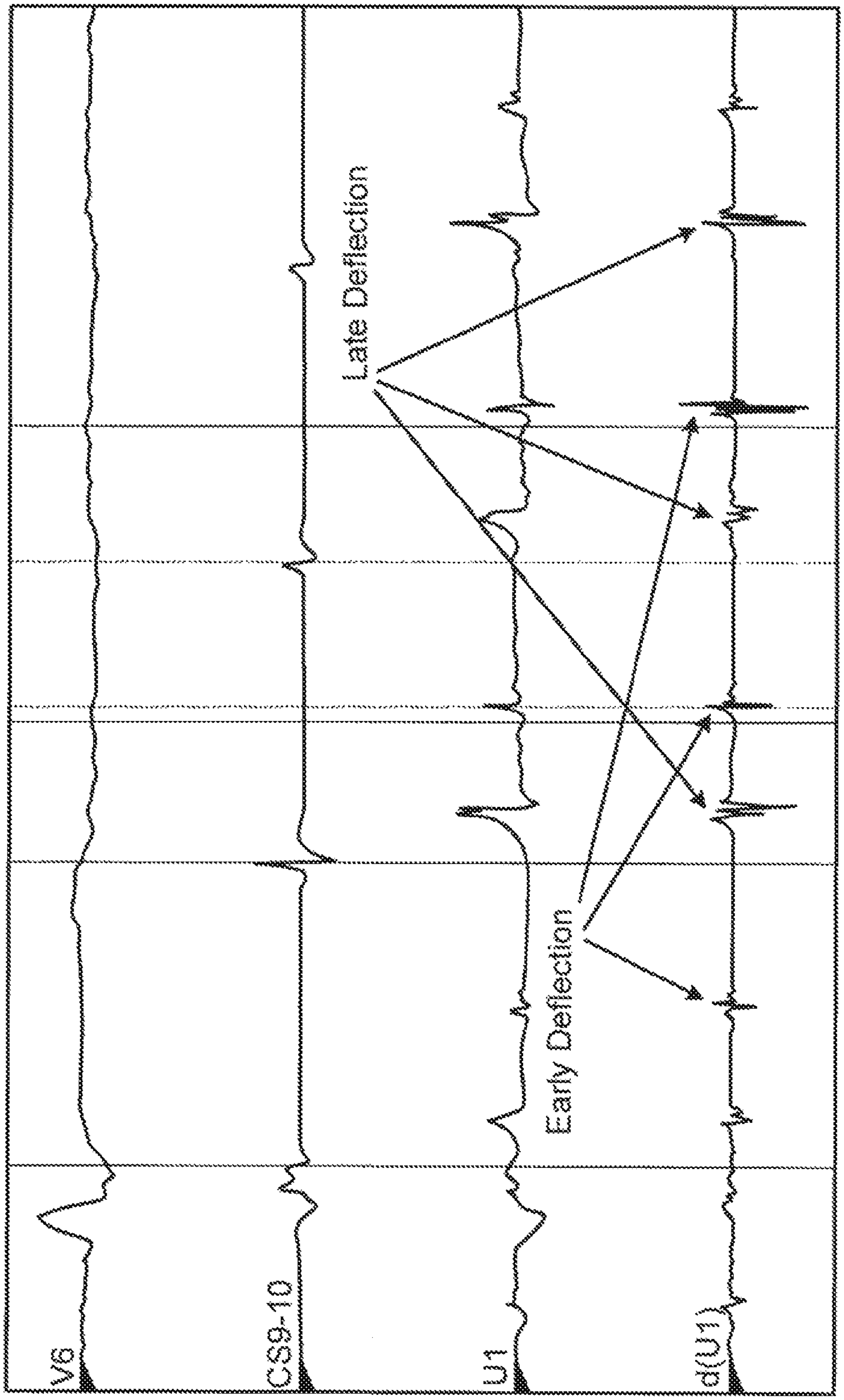
FIGS. 9 and 10 show exemplary data signals for annotation determinations.
Figure 10:
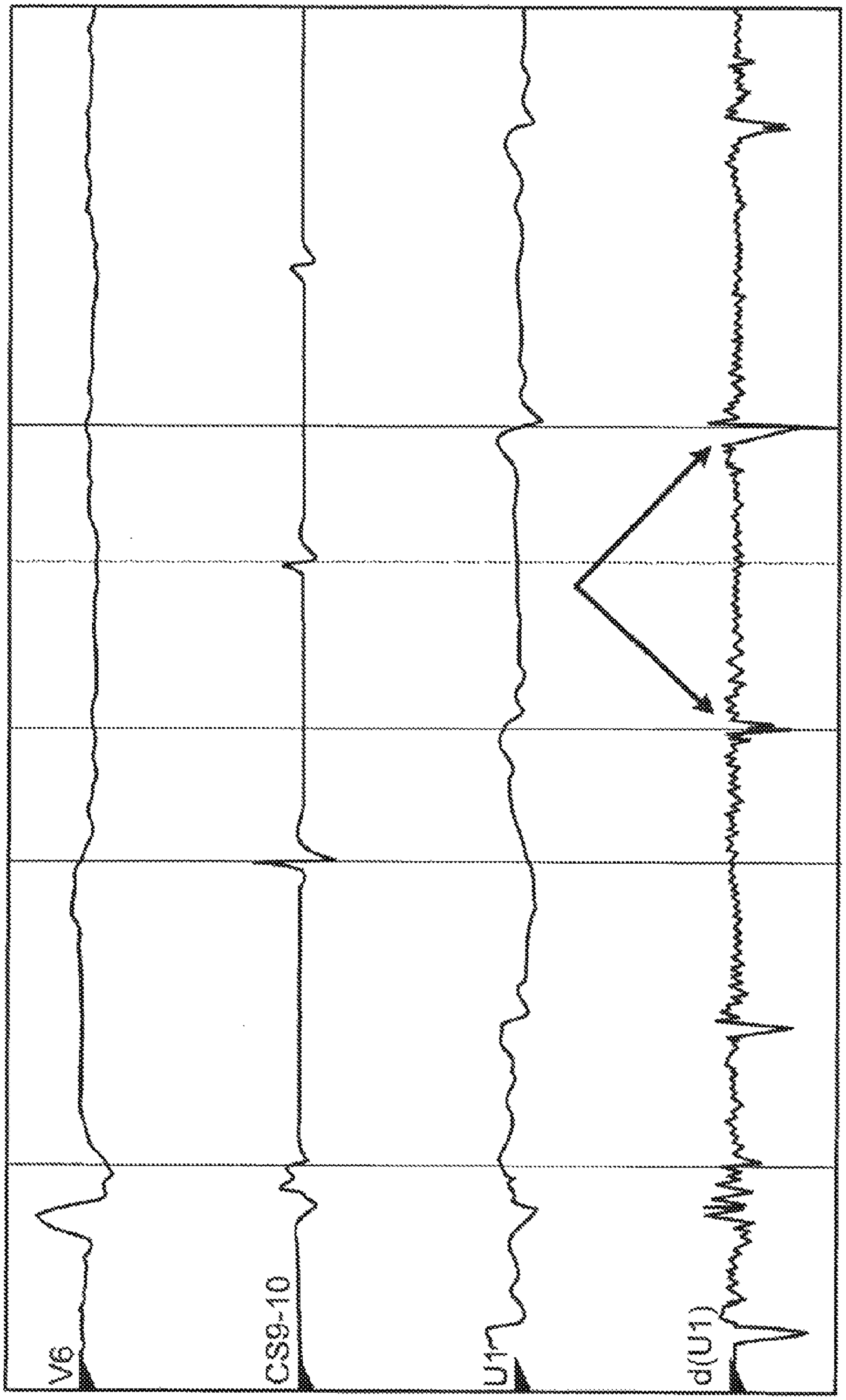

FIG. 9 and FIG. 10 show 4 waveforms collected from a human patient. Going from top to bottom, the first waveform is ECG lead V6, the second waveform is a bipolar recording from CS electrodes 9-10, the third waveform is a unipolar electrotram in the mapping site and the forth waveform is the time derivative of the unipolar recording. FIG. 9 shows three beats in one location near a line of block (the first common condition). The minimum unipolar electrogram slope, used in this case as timing annotation, alternates between the earlier and later deflection between beats. This occurs despite minimal catheter motion and a stable rhythm.

FIG. 10 shows a beat where both the current and next activation just fall within the beat window (the second common condition). Automatic timing annotation may take the early or late timing depending on which deflection happens to be larger.

When manually annotating activation time, experienced operators consider both the electrogram being annotated and the surrounding activation times to create a consistent and physiologically plausible map. The method described below performs a similar function automatically.

Spatial Consistency Method

The Spatial Consistency Method provides a way for the computer system to automatically reduce spatial variation in annotations in a way that is consistent with the individual electrograms and with an adjustable degree of variation reduction.

This method has three stages:

(a) Individual electrogram analysis, (b) Electrogram clustering, and (c) Annotation adjustment.

Individual Electrogram Analysis

During this step, each electrogram is analyzed by the computer system using the annotation criteria previously described to extract annotation candidates. The annotation criteria define what aspects of the signal are used to determine activation and prescribe a minimum activation threshold. An annotation candidate is an electrogram sample that exceeds the annotation threshold and is a local annotation criteria extrema. Electrograms without annotations candidates are considered to have no activation.

The computer system assigns a confidence value to every annotation candidate of every electrogram. Many possible mappings from electrogram characteristics to confidence values are possible. In one exemplary method, the mapping maintains three properties:

(a) Stronger deflections should have higher confidences;

(b) Similar strength deflections should have similar confidences across all electrograms; and (c) The numerical difference between confidence values should correspond to the likelihood that higher confidence value is preferred.

One way to do this mapping is for the computer system to normalize the annotation criteria amplitude to the range of annotation criteria amplitudes observed across all electrograms at samples that exceed the detection threshold. This mapping is believed to fulfill the first two properties enumerated above and adequately represents the third property.

If degree of variation reduction is zero, the computer system selects the annotation candidate with the highest confidence value for each electrogram for the annotation for that electrogram. If the some variation reduction is enabled, the computer system uses the confidence values during the annotation adjustment to reduce spatial variation.

Electrogram Clustering

For each electrogram included in the map, a set of neighboring electrograms (e.g., spatially neighboring electrograms or electrograms within a predetermined distance from one another) and associated weights are defined. One way of automatically defining these sets by the computer system is to include all electrograms whose projected location is within a specified distance (e.g., a radius of inclusion or radius of influence) of the projected location of each electrogram included in the map. A variety of associated weighting functions could be used. One option is the inverse of the distance; another is the cosine of the ratio of the distance to the maximum distance. Both these methods are used in the iterative annotation adjustment as described below.

Annotation Adjustment

Annotation adjustment is a computer implemented optimization procedure that improves spatial consistency to the target amount by automatically identifying and changing the least certain annotations first. The goal is that annotations for electrograms with multiple weak deflections should migrate from the strongest deflection to the deflection that is closest to consistent with neighboring annotations as the target degree of spatial consistency is increased. This produces an increasingly smooth map while changing the annotations that are most likely to be erroneous.

The optimization problem is implemented by the computer system and involves a large number of coupled variables (one variable per electrogram annotation, which depends on the annotations of all electrogram's neighbor) and is highly non-linear (each annotation can only take a discrete set of values, and those values vary significantly across the map and between neighbors).

To solve this problem in a tractable duration, a greedy iterative algorithm can be used. This algorithm includes four steps:

(a) The computer system initializes all annotations with the highest confidence candidate or marked as no annotation if no candidate exists.

(b) For each annotation, the computer system combines neighboring annotations to produce an estimate of the annotation. This uses an interpolation function from the neighboring annotations to the current annotation.

(c) For each annotation, the computer system computes the cost associated with switching from the current annotation to the interpolated annotation.

(d) Based on the calculated costs, the computer system selects the lowest cost annotation change and replaces that annotation with the interpolated value. Increment the aggregate cost by the cost associated with this adjustment. Update the interpolated annotations for neighboring annotations. Repeat this step while the aggregate cost is less than the target total cost, which is based on the target degree of spatial consistency.

For the interpolation function, a number of formulations are possible. One formulation is inverse distance weighting with snapping to the closest candidate. For reentrant maps, the interpolation should evaluate the base interpolation function twice for early and late points, once while treating all points as early and once as late.

Many cost functions that combine the candidate confidences in various ways may be applied to this problem. One method is to take the arithmetic difference between the confidences.

This iterative algorithm incrementally "smoothes" the annotations by moving the least certain annotations first but only to acceptable electrogram features.

Figure 11:
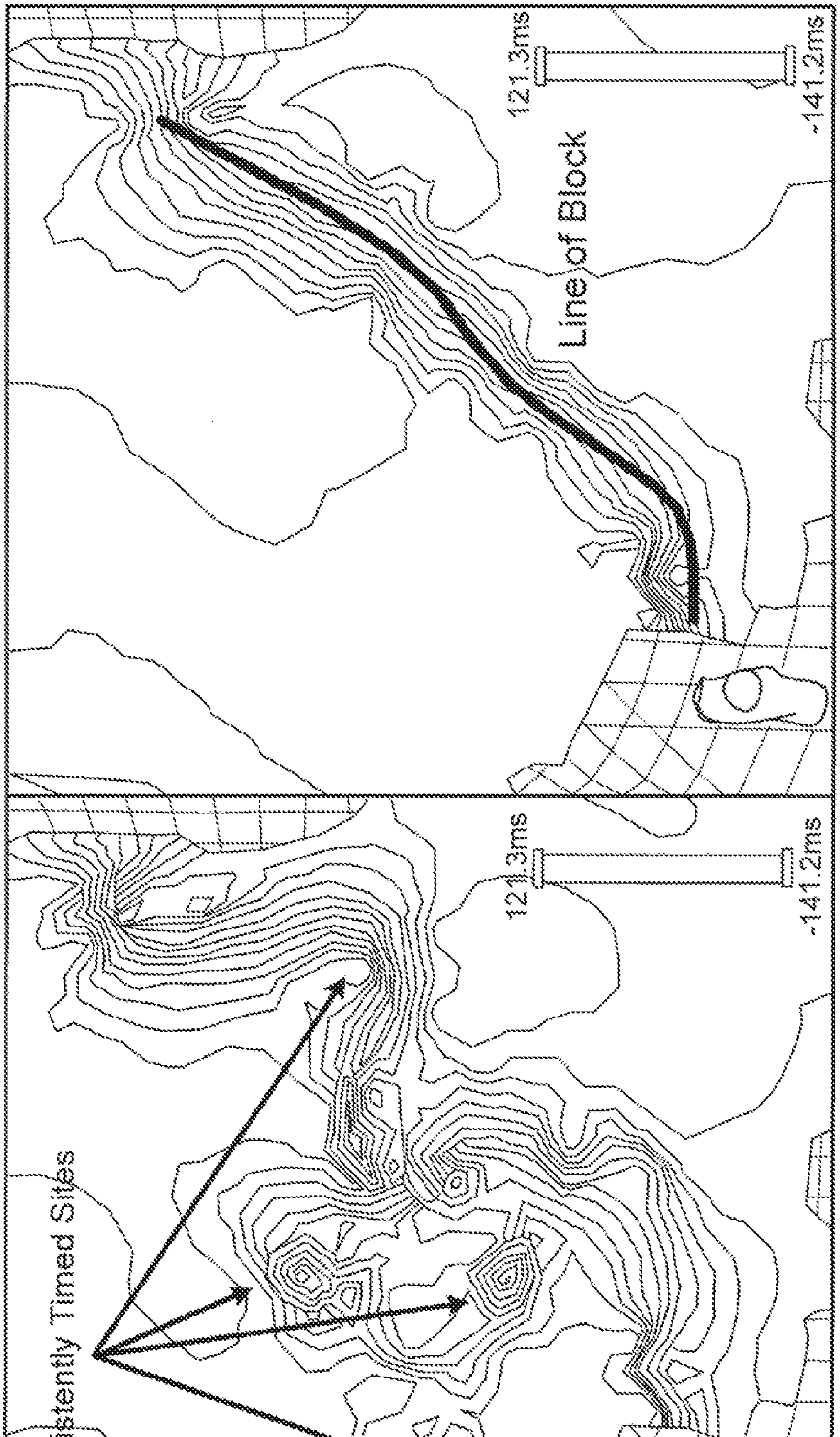
FIG. 11 shows exemplary electro-anatomical maps.

FIG. 11 shows an example of applying this method to an activation map. The arrows indicate a number of electrogram sites with double activations that are incorrectly timed before applying the spatial consistency operation. After applying this operation, the map shows a clearly defined line of block that is physiologically plausible.

Automatic Categorical Annotation

Certain electrogram categories are of particular clinical significance when constructing an electroanatomical map. Since the operator is unable to manually review each point in the surface map data, it is important to automatically annotate those categories by the computer system. These include electrograms with double deflections, multiple deflections, fractionation, and/or no activation.

Automatically annotating electrograms with these categories assists the user in quickly finding regions of interest.

A number of methods of using the computer system to automatically divide electrograms into these categories are possible. All of these methods share the overall goal of segmenting the electrogram into regions with and without activation and then categorizing based on those segments. One method includes:

(a) For each electrogram, the computer system marks each sample of the electrogram that exceeds the activation threshold for the annotation criteria. The act of marking indicates that the sample of the electrogram is considered to during a period of activation.

(b) For each marked sample of each electrogram, the computer system marks adjacent samples within a specified window (maximum same activation duration). This fills in small gaps that arise, for example, as the activation detection signal transitions from positive to negative.

(c) For each electrogram, the computer system finds all the sequences of contiguous unmarked samples that are longer than a second specified window (minimum distinct activation separation). These are the periods of no activation. Discard any period that begins at the start of the electrogram or ends at the end of the electrogram as these periods are not between activations.

(d) For each electrogram, the computer system finds all the sequences of contiguous marked samples that are longer than a third specified window (minimum fractionation duration).

(e) The computer system categorizes the electrogram according to the following rules:

If samples are marked, the electrogram has no activation.

If a contiguous marked sequence longer than the minimum fractionation duration exists, the electrogram is fractionated.

If one contiguous unmarked sequence longer than the minimum distinct activation separation exists between marked samples, the electrogram has a double deflection.

If more than one contiguous unmarked sequence longer than the minimum distinct activation separation exists between marked samples, the electrogram has multiple deflections.

Otherwise, the electrogram is a normal activation.

Figure 12:
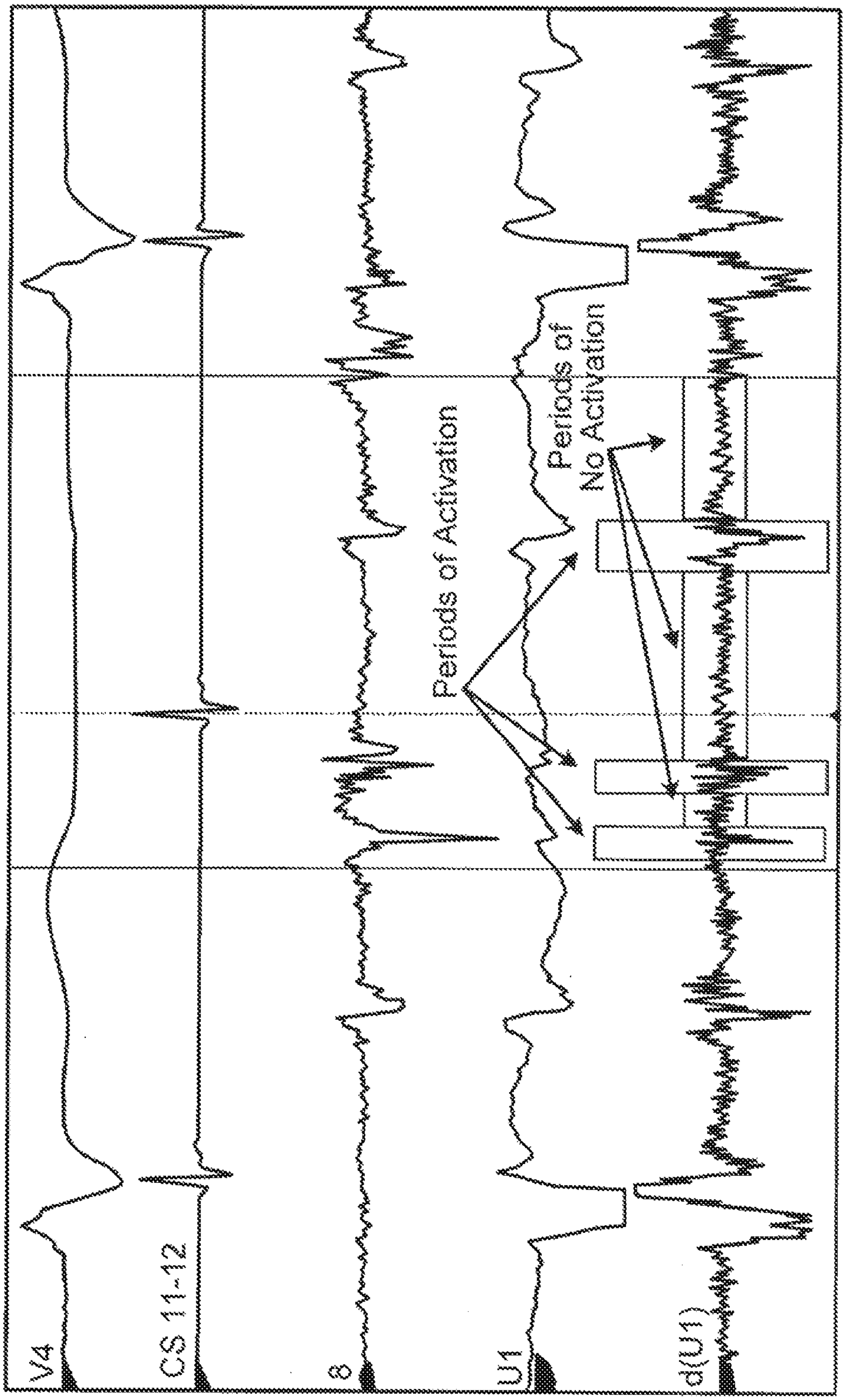
FIG. 12 shows exemplary data signals for annotation determinations.

FIG. 12 depicts this process for an electrogram with three deflections. "U" is the unipolar and "B" is the bipolar electrogram. The first and second step of the method above mark the electrogram samples within the tall boxes because some of those samples exceed the activation threshold. The third step segments out the three short boxes. The last of these is discarded because it is at the end of the cycle. Since two sufficiently long period of no activation exist, the method annotates this electrogram as a multiple deflection.

Because this annotation is intended to focus attention on specific sites for manual inspection, false positives for double deflections, multiple deflections, and fractionation should be minimized. One method of reducing the false positive rate is to use a higher activation threshold (the multiple activation threshold) when marking samples for these annotations. This threshold may be determined by scaling the activation threshold by an adjustable ratio. Furthermore, the annotation criteria for no activation, fractionation, and counting deflections need not be the same.

User Input Propagation

Automatic methods may not always annotate electrograms in the way desired by users. Therefore, user input in the form of manual annotation may be provided in addition to the annotations automatically generated by the computer system. A manual annotation is also designated manual override, because it locally overrides the computers automated decision. Because neighboring electrograms are likely to be similarly annotated, propagation of manual overrides to neighboring electrograms by the computer system can dramatically reduce the number of electrograms that must be manually annotated.

Two types of manual overrides that can be automatically propagated by the computer system include categorical annotation overrides such as tagging as no activation and value annotation overrides such as changing activation time.

Categorical Annotation Overrides

For this type of override, a categorical annotation such as no activation, double deflection, or fractionation is changed from the original automatically generated annotation by the user for a particular electrogram. The override may specify normal activation to remove an automatic categorization such as double deflection that was incorrectly determined. The computer system applies the same categorical annotations to neighboring electrograms (e.g., spatially correlated electrograms) with similar characteristics.

Propagating categorical overrides includes three functions:

(a) Electrogram clustering, (b) Electrogram annotation method change and (c) Conflict resolution rule.

Electrogram Clustering

Electrogram clustering for categorical overrides can use the same methods as described above for the spatial consistency method. Since each categorical override is manually determined, a separate radius of influence could be specified for each override. For example, a separate distance to the specified measured signal could be specified for each override.

Electrogram Annotation Method Change

To bias the automatic annotation system towards the manual override near the overridden electrogram, some aspect of the automatic annotation system must be changed for the neighboring electrograms. Two basic approaches exist for this alteration: locally altering annotation criteria such as the activation threshold and locally altering the confidences used by the spatial consistency method.

For the approach of changing annotation criteria, for each type of categorical override the computer system adjusts annotation criteria in an appropriate way for electrograms within the associated cluster. This degree of the adjustment may be adjustable and the strength of this adjustment can be a function of distance from the overridden electrogram. One possible set of modification methods is as follows:

For a no activation override, the computer system increases the activation threshold (and, if implemented, the multiple activation threshold) for neighboring electrograms by an adjustable percentage that declines as a function of distance between the overridden location and the neighbors. The computer system then re-determines the annotations for the neighboring electrograms based on the adjusted activation threshold.

For a double deflection, multiple deflection, or fractionation override, the computer system decreases the activation threshold (and, if implemented, the multiple activation threshold) for neighboring electrograms by an adjustable percentage that declines as a function of distance. The computer system then re-determines the annotations for the neighboring electrograms based on the adjusted activation threshold.

For a normal activation override, the computer system decreases the activation threshold (and, if implemented, increase the multiple activation threshold) for neighboring electrograms by an adjustable percentage that declines as a function of distance. The computer system then re-determines the annotations for the neighboring electrograms based on the adjusted activation threshold.

Numerous functions may be used to change the adjustment amount as a function of distance. One such function is one plus cosine of π times the ratio of the distance between the electrograms and the maximum distance included in the cluster.

For all of these adjustments, an alternative to applying a fixed adjustment is to find the appropriate activation threshold to qualify the overridden electrogram for the selected category, and then apply a distance attenuated version of that threshold to the neighboring electrograms.

The approach of changing confidences works similarly to the approach of changing annotation criteria except the confidences are adjusted as follows:

For electrograms near a no activation override, if the confidence is above an adjustable threshold, the confidence is not changed by the computer system and the electrogram is considered as activated and is timed normally. If the confidence is below the threshold, the confidence is set to zero by the computer system and the electrogram is considered as not activated.

For electrograms near an activation override that were determined to be activating by the automatic system, the electrogram is treated normally except the timing annotation may be adjusted by the methods described below for value annotation overrides.

For electrograms near an activation override that were determined to not be activating by the automatic system, the electrogram is considered to have small, uniform confidence. This forces the electrogram to be timed by the computer system in a way that is consistent with the neighboring electrograms that have activation. If spatial consistency is not enabled, the electrogram is annotated at the largest annotation candidate, even if that sample does not exceed threshold.

Conflict Resolution Rule

Conflict resolution is necessary when an electrogram is within the neighborhoods of two or more possibly inconsistent categorical overrides. The conflict resolution rule determines how the computer system combines the multiple overrides to effect electrograms within their radii of influence and/or their set distances.

One method is to simply have the computer system consider the closest override and ignore the rest when annotating each electrogram.

A second method is to have the computer system combine the effects of the overrides on either the activation thresholds or the confidences according to a function such as inverse distance weighting.

Value Annotation Overrides

For this type of override, an annotation with a range of possible values such as activation time is manually set for a particular electrogram. Neighboring electrograms with similar characteristics should be influenced by the overridden annotation (e.g., the computer system determines the annotation for the neighboring electrograms based in part on the override). For example, a region may have numerous electrograms with similar double deflections. When the user manually moves the activation time from one deflection to another, the computer system should modify the surrounding electrograms to follow suit.

This problem is closely related to the spatial consistency. One way of solving this problem is by extending the spatial consistency method to respect manual annotations. This extension can be made by preceding the first step of the annotation adjustment method given for spatial consistency with the following steps:

For each overridden electrogram, the computer system sets the confidence to the highest possible level at the overridden sample and sets all other confidence values to no confidence. This prevents the overridden annotation from changing.

For neighboring electrograms that are not activating according to the automatic criteria, the computer system sets the confidence to a small, uniform value and initialize the annotation with the override value. This ensures the electrogram is timed consistently with surrounding points because it can change freely away from the initial value.

For neighboring electrograms that are activating according to the automatic criteria, the computer system uses a biased confidence for all computations and optionally initializes the annotation at the highest confidence sample within a given window around the override value. This starts the annotation close to the override and increases the likelihood that the annotation will stay close to the override but still allows the annotation to move back to the unbiased value if that activation is sufficiently strong.

The biased confidences are the automatic confidences adjusted by the computer system to account for the neighboring manual overrides. A number of functions could be used to compute the biased confidence. One such function is adding to the baseline confidence a value that starts with an adjustable base strength and attenuates that strength as a function of distance from the override and time difference between the sample associated with the confidence and the override value. The attenuation functions could be of many forms; one form is a raised cosine of the ratio of the distance or time difference to the maximum distance or time difference.

Figure 13:
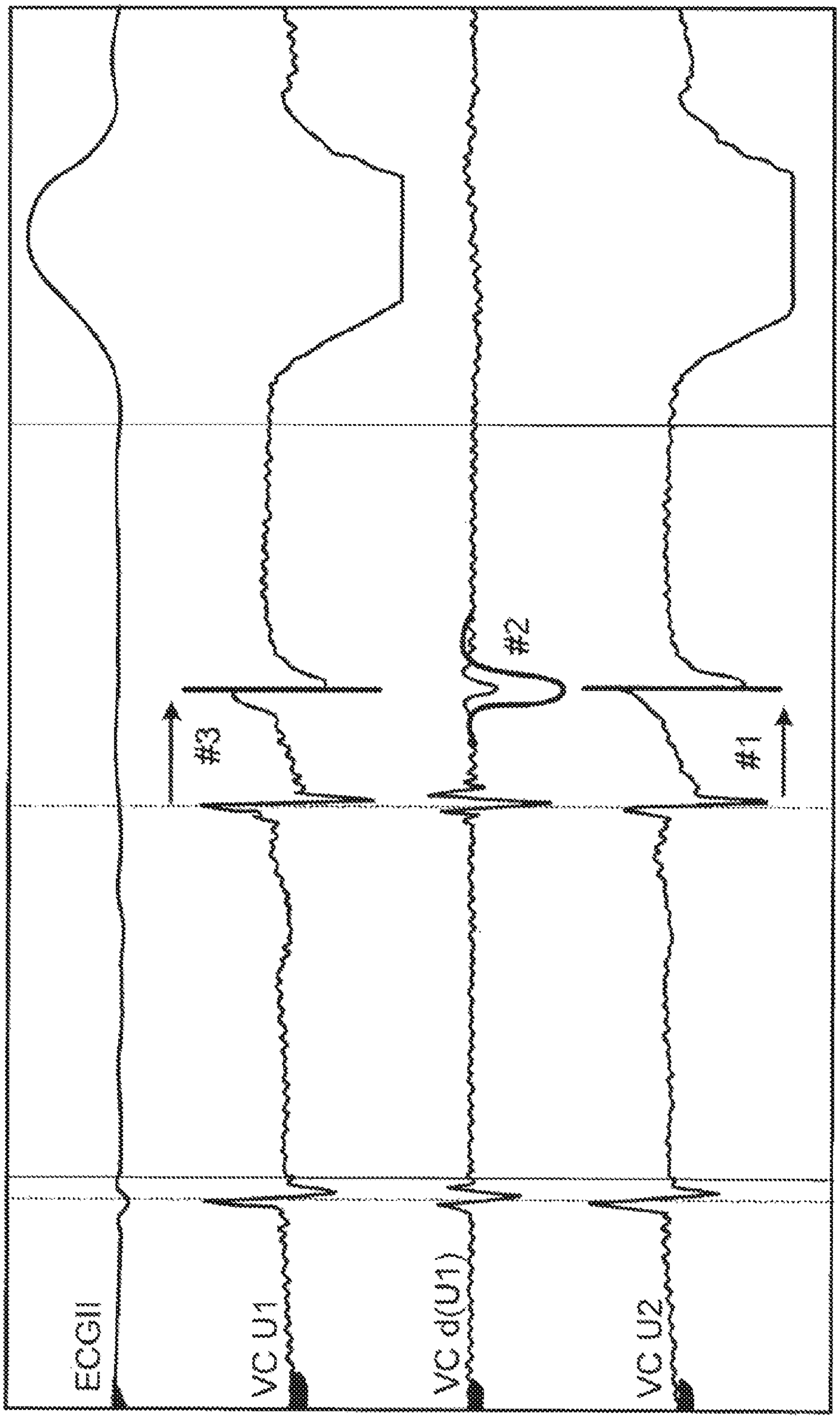
FIG. 13 shows exemplary data signals for annotation determinations and adjustments.

An example of this process is shown FIG. 13. "U1" and "U2" are neighboring unipolar electrograms. Manual annotation of U2 from the automatically selected early time to the later time (step #1) will increase the confidence associated with the smaller minima in the d(U1) trace (step #2), thereby adjusting the timing of U1 to the later time (step #3).

Surface Map Interpolation

Once surface data has been annotated, the computer system displays the surface data to the operator. For example, the annotated data may be presented in color or using any of a number of textures on surface geometry. In the case of using an inverse Laplace operator to generate map surface data, the resultant dataset can have values on every point on the surface geometry and no further surface interpolation is necessary.

In the case of using finding points on the chamber, a surface interpolation scheme may be necessary. For example, surface interpolation may take all annotation values in the surface map data and provide an interpolate value for them on each of the vertices used to represent the surface. The surface interpolation can follow any of a number of schemes including 3D Kriging, or Mean Value Interpolation explained in Tao Ju, Scott Schaefer, and Joe Warren. 2005. Mean value coordinates for closed triangular meshes. ACM Trans. Graph. 24, 3 (July 2005), 561-566.

Representative System

Figure 14:
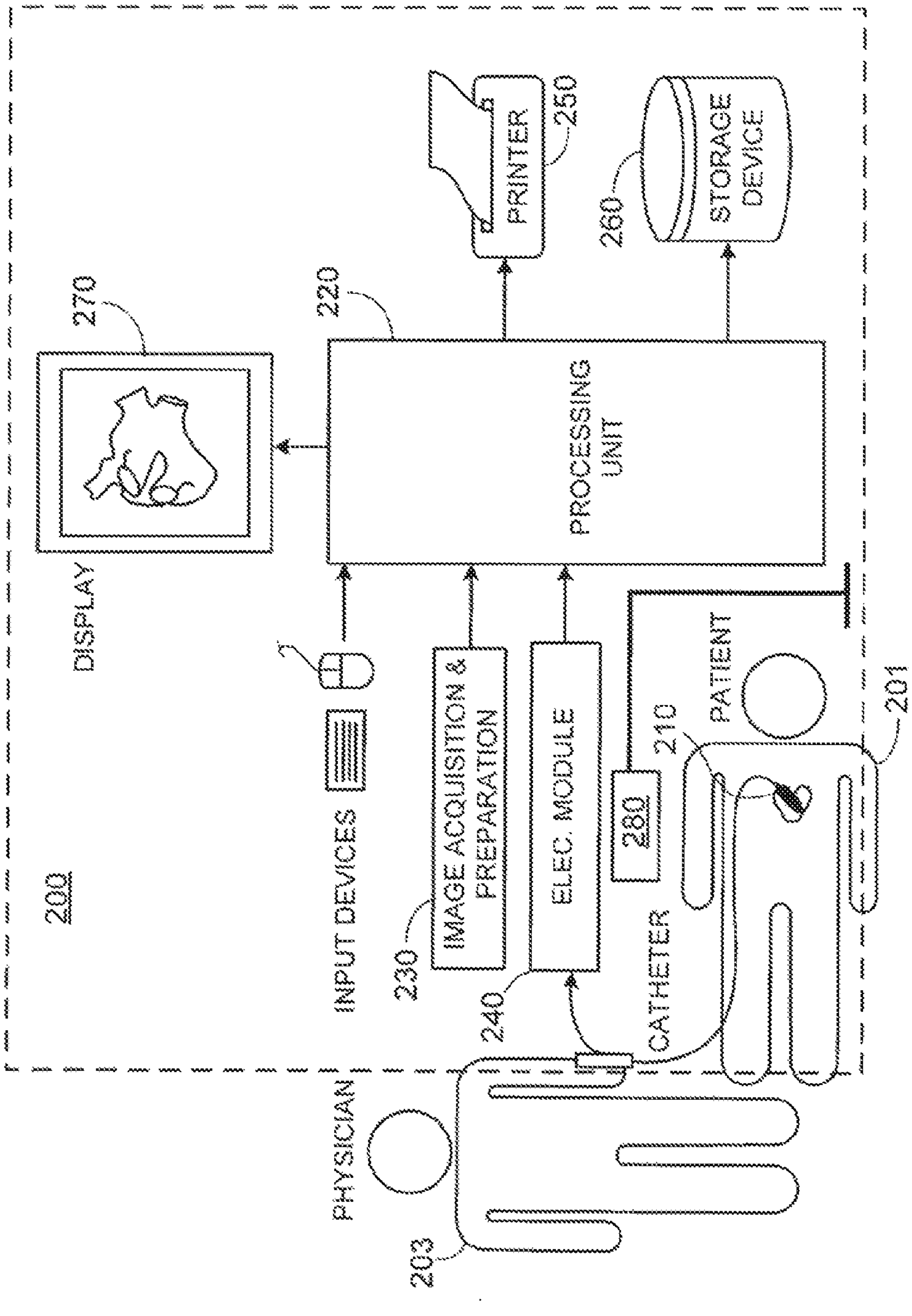
FIG. 14 shows a schematic diagram of an exemplary system.

FIG. 14 shows a schematic diagram of an exemplary embodiment of a non-contact system 200. The non-contact system 200 includes a moveable catheter 210 having multiple spatially distributed electrodes. During the signal acquisition stage of the non-contact mapping procedure the catheter 210 is displaced to multiple locations within the heart chamber into which catheter 210 is inserted.

In some embodiments the distal end of the catheter 210 is fitted with multiple electrodes spread somewhat uniformly over the catheter. For example, the electrodes may be mounted on the catheter 210 following a 3D olive shape. The electrodes are mounted on a device capable of deploying the electrodes into the desired shape while inside the heart, and retracting the electrodes when the catheter is removed from the heart. To allow deployment into a 3D shape in the heart, electrodes may be mounted on a balloon, or shape memory material such as Nitinol.

At each of the locations to which the catheter 210 is moved, the catheter's multiple electrodes acquire signals resulting from the electrical activity in the heart cavity. Consequently, reconstructing and presenting to a user (such as a doctor and/or technician) physiological data pertaining to the heart's electrical activity may be based on information acquired at multiple locations, thereby providing a more accurate and faithful reconstruction of physiological behavior of the endocardium surface. The acquisition of signals at multiple catheter locations in the heart chamber enables the catheter to effectively act as a "mega-catheter" whose effective number of electrodes and electrode span is proportional to the product of the number of locations in which signal acquisition is performed and the number of electrodes the catheter has.

To enhance the quality of the reconstructed physiological information at the endocardium surface, in some embodiments the catheter 210 is moved to more than three locations (for example, more than 5, 10, or even 50 locations) within the heart chamber. Further, the spatial range over which the catheter is moved may be larger than one third (⅓) of the diameter of the heart cavity (for example, larger than 35%, 40%, 50% or even 60% of the diameter of the heart cavity). Additionally, in some embodiments the reconstructed physiological information is computed based on signals measured over several heart beats, either at a single catheter location within the heart chamber or over several locations. In circumstances where the reconstructed physiological information is based on multiple measurements over several heart beats, the measurements are synchronized with one another so that the measurement are performed at approximately the same phase of the heart cycle. The signal measurements over multiple beats can be synchronized based on features detected from physiological data such as surface ECG or intracardiac electrograms.

Non-contact mapping system 200 further includes the processing unit 220 which performs several of the operations pertaining to the non-contact mapping procedure, including the reconstruction procedure to determine the physiological information at the endocardium surface (e.g., as described above). To expedite the computational operations performed by the non-contact mapping system 200, the processing unit 220 can compute, generally prior to the insertion of the catheter into the heart chamber and/or before signal acquisition by the catheter's electrodes has commenced, transformation functions that can be used in real-time to facilitate the reconstruction process. Once the catheter 210 is inserted and is displaced to a particular location in the heart chamber, the mapping procedure can be performed expeditiously by computing in real-time those transformation components that were not computed ahead of the signal acquisition stage, and combining those components with the appropriate pre-processed transformation components to obtain the overall transformation function(s). That overall transformation function is applied to the acquired raw data to perform the inverse reconstruction operation.

The processing unit 220 also performs a catheter registration procedure. The location of the catheter 210 inserted into the heart chamber can be determined using a conventional sensing and tracking system (not shown) that provide the 3D spatial coordinates of the catheter and/or its multiple electrodes with respect to the catheter's coordinate system as established by the sensing and tracking system. However, to perform the mapping procedure and reconstruct physiological information on the endocardium surface, it is necessary to align the coordinate system of the catheter 210 with the endocardium surface's coordinate system. The processing unit 220 (or some other processing module of system 200) determines a coordinate system transformation function that transforms the 3D spatial coordinates of the catheter's locations into coordinates expressed in terms of the endocardium surface's coordinate system, or vice-versa.

The processing unit 220 also performs post-processing operations on the reconstructed physiological information to extract and display useful features of the information to the operator of the system 200 and/or other persons (e.g., a physician).

As further shown in FIG. 8, the signals acquired by the multiple electrodes of catheter 210 are passed to the processing unit 220 via the signal conditioning module 240. The signal conditioning module 240 receives the signals communicated from the catheter 210 and performs signal enhancement operations on the signals before they are forwarded to the processing unit 220. Signal conditioning hardware is used to amplify, filter and continuously sample intracardiac potential measured by each electrode. The intracardiac signals typically have a maximum amplitude of 60 mV, with a mean of a few millivolts. In some embodiments the signals are bandpass filtered in a frequency range (e.g., 0.5-500 Hz) and sampled with analog to digital converters (e.g., with 15-bit resolution at 1 kHz). To avoid interference with electrical equipment in the room, the signal can be filtered to remove the frequency corresponding to the power supply (e.g., 60 Hz). Other types of signal processing operations such as spectral equalization, automatic gain control, etc. may also take place. The resultant processed signals are forwarded by the module 240 to the processing unit 220 for further processing.

As further shown in FIG. 14, the non-contact mapping system 200 also includes peripheral devices such as printer 250 and/or display device 270, both of which are interconnected to the processing unit 220. Additionally, the mapping system 200 includes storage device 260 that is used to store data acquired by the various interconnected modules, including the volumetric images, raw data measured by electrodes and the resultant endocardium representation computed there from, the partially computed transformations used to expedite the mapping procedures, the reconstructed physiological information corresponding to the endocardium surface, etc.

Other Embodiments

The methods and systems described herein are not limited to a particular hardware or software configuration, and may find applicability in many computing or processing environments. The methods and systems can be implemented in hardware, or a combination of hardware and software, and/or can be implemented from commercially available modules applications and devices. Where the implementation of the systems and methods described herein is at least partly based on use of microprocessors, the methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted. The device(s) or computer systems that integrate with the processor(s) can include, for example, a personal computer(s), workstation (e.g., Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a microprocessor" and "a processor", or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network using a variety of communications protocols, and unless otherwise specified, can be arranged to include a combination of external and internal memory devices, where such memory can be contiguous and/or partitioned based on the application. Accordingly, references to a database can be understood to include one or more memory associations, where such references can include commercially available database products (e.g., SQL, Informix, Oracle) and also proprietary databases, and may also include other structures for associating memory such as links, queues, graphs, trees, with such structures provided for illustration and not limitation.

Accordingly, other embodiments are within the scope of the following claims.

We claim:

1. A method for providing information about a patient's heart, the method comprising:

measuring signals using one or more electrodes over a time period including multiple heart beat cycles, at least some of the signals being in response to electrical activity in the patient's heart cavity;

generating, by a computer, annotation information for the measured signals by applying one or more operators to a specified measured signal and one or more spatially and/or temporally neighboring measured signals; and generating, by the computer, an electroanatomical representation of the patient's heart that includes at least some of the annotation information.

2. The method of claim 1, wherein generating the annotation information comprises applying one or more operators to the measured signals to identify at least one of regions of the heart having double deflections, regions of the heart having multiple deflections, regions of the heart having fractionation, regions of the heart having double activation, and regions of the heart having no activation.

3. The method of claim 1, further comprising:

receiving, from an operator, a change to the annotation information for a specified measured signal; and modifying, by the computer, annotation information for one or more additional measured signals based on the change.

4. The method of claim 3, wherein modifying the annotation information for one or more additional measured signals comprises automatically adjusting annotation information for one or more additional measured signals in proximity to the specified measured signal.

5. The method of claim 4, wherein the measured signals in spatial proximity to the specified measured signal comprise signals at positions with a set distance to the specified measured signal.

6. The method of claim 5, wherein applying the algorithm to the selected portions of the first signal to determine the triggering event comprises applying an algorithm to integrate the first signal over a window.

7. The method of claim 1, wherein the signals measured at the one or more electrodes comprise electrograms.

8. The method of claim 7, further comprising:

receiving, from an operator, a change to the annotation information for a specified electrogram; and automatically, by the computer, adjusting the annotation information for other electrograms based on the operator change to the annotation information for the specified electrogram.

9. The method of claim 1, wherein spatially neighboring electrograms comprise electrograms within a predefined distance.

10. The method of claim 1, wherein generating the annotation information comprises:

for electrograms including multiple deflections, selecting a deflection of the multiple deflections based on timing information for the multiple deflections and timing information for deflections in spatially neighboring electrograms; and using the selected deflection to determine the annotation information.

11. The method of claim 1, wherein generating the annotation information comprises generating annotation information for a specific location of the endocardium based on the signals measured at an electrode location corresponding to the specific location and signals measured at one or more additional electrodes at locations in spatial proximity to the electrode location corresponding to the specific location.

12. The method of claim 11, wherein one or more additional electrodes at locations in spatial proximity to the specific location comprise one or more additional electrodes with a predefined distance of the specific location.

13. The method of claim 1, wherein generating the annotation information comprises generating annotation information for a specific location of the endocardium based on the signals measured at an electrode location corresponding to the specific beat and signals measured at one or more previous beats at the same electrode.

14. The method of claim 1, wherein generating the annotation information comprises using spatial information about the positions at which the signals were measured to determine local timing information.

15. The method of claim 1, wherein the one or more electrodes comprise one or more electrodes on an intracardiac catheter.

16. The method of claim 1, further comprising using the electroanatomical representation of a patient's heart to guide treatment of the heart activity.

17. The method of claim 1, further comprising selecting a subset of less than all of the signals and generating an electroanatomical representation of the patient's heart based on the selected subset of less than all of the signals.

18. A system for providing information about a patient's heart, the system comprising:

one or more electrodes for measuring signals at multiple positions in the heart cavity, at least some of the signals being in response to electrical activity in the patient's heart cavity; and an electronic processor coupled to the one or more electrodes, wherein the electronic processor is configured to:

generate annotation information for the measured signals by applying one or more operators to a specified measured signal and spatially and/or temporally neighborhood measured signals; and generate an electroanatomical representation of the patient's heart that includes at least some of the annotation information.

19. The system of claim 18, further comprising selecting a subset of less than all of the signals and generating an electroanatomical representation of the patient's heart based on the selected subset of less than all of the signals.

20. A system for providing information about a patient's heart, the system comprising:

one or more electrodes for measuring signals at multiple positions in the heart cavity, at least some of the signals being in response to electrical activity in the patient's heart cavity; and an electronic processor coupled to the one or more electrodes, wherein the electronic processor is configured to:

select a subset of less than all of the signals;

generate annotation information for the measured signals by applying one or more operators to a specified measured signal and spatially and/or temporally neighborhood measured signals; and generate, based on the selected subset of less than all of the signals, an electroanatomical representation of the patient's heart that includes at least some of the annotation information.

* * * * *